(12) United States Patent
Park et al.

(10) Patent No.: US 9,757,580 B2
(45) Date of Patent: Sep. 12, 2017

(54) CONTROLLER, AND PATCH TYPE AUTOMATED EXTERNAL DEFIBRILLATOR FOR CONTROLLING DEFIBRILLATION USING THE SAME

(71) Applicants: Sang Wook Park, Hwaseong-si (KR); Hyung Jong Ko, Seongnam-si (KR); Yong In Park, Seoul (KR); Seoung Jae Yoo, Seongnam-si (KR); Yun Cheol Han, Yongin-si (KR)

(72) Inventors: Sang Wook Park, Hwaseong-si (KR); Hyung Jong Ko, Seongnam-si (KR); Yong In Park, Seoul (KR); Seoung Jae Yoo, Seongnam-si (KR); Yun Cheol Han, Yongin-si (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 0 days.

(21) Appl. No.: 15/087,353

(22) Filed: Mar. 31, 2016

(65) Prior Publication Data
US 2016/0325107 A1    Nov. 10, 2016

(30) Foreign Application Priority Data

May 8, 2015    (KR) ........................ 10-2015-0064783

(51) Int. Cl.
| | |
|---|---|
| *A61N 1/00* | (2006.01) |
| *A61N 1/39* | (2006.01) |
| *A61N 1/04* | (2006.01) |
| *A61B 5/11* | (2006.01) |
| *A61N 1/362* | (2006.01) |

(Continued)

(52) U.S. Cl.
CPC .......... *A61N 1/3987* (2013.01); *A61B 5/1117* (2013.01); *A61N 1/046* (2013.01); *A61N 1/0492* (2013.01); *A61N 1/3621* (2013.01); *A61N 1/3925* (2013.01); *A61N 1/3968* (2013.01); *A61N 1/3975* (2013.01); *A61B 5/046* (2013.01); *A61B 5/0432* (2013.01); *A61B 5/0464* (2013.01);

(Continued)

(58) Field of Classification Search
CPC .. A61N 1/3987; A61N 1/3968; A61N 1/0492; A61N 1/392
See application file for complete search history.

(56) References Cited

U.S. PATENT DOCUMENTS

| | | |
|---|---|---|
| 5,078,134 A | 1/1992 | Heilman et al. |
| 8,565,871 B2 | 10/2013 | Tuysserkani |

(Continued)

FOREIGN PATENT DOCUMENTS

| | | |
|---|---|---|
| JP | 20120235874 | 12/2012 |
| KR | 20100042676 A | 4/2010 |

(Continued)

*Primary Examiner* — Robert N Wieland
(74) *Attorney, Agent, or Firm* — Volentine & Whitt, PLLC

(57) ABSTRACT

A wearable patch-type automatic defibrillator attachable to a region of a patient near the patient's heart includes a battery which stores electrical energy for defibrillation, a controller which controls the battery, electrocardiogram (ECG) electrodes, and defibrillation electrodes. The controller analyzes ECG signals of the patient received through the ECG electrodes, and automatically provides the patient with the electrical energy stored in the battery through the defibrillation electrodes when defibrillation is needed according to a result of the analysis.

18 Claims, 18 Drawing Sheets

(51) Int. Cl.
  *A61B 5/00*    (2006.01)
  *A61B 5/0432*  (2006.01)
  *A61B 5/046*   (2006.01)
  *A61B 5/0464*  (2006.01)

(52) U.S. Cl.
  CPC ..... *A61B 5/6833* (2013.01); *A61B 2562/0219* (2013.01)

(56) References Cited

U.S. PATENT DOCUMENTS

| | | |
|---|---|---|
| 8,577,475 B2 | 11/2013 | Bowers |
| 8,838,235 B2 | 9/2014 | Cowan et al. |
| 2006/0173498 A1* | 8/2006 | Banville ............ A61N 1/39 607/5 |
| 2006/0224072 A1 | 10/2006 | Shennib |
| 2007/0032830 A1 | 2/2007 | Bowers |
| 2010/0016746 A1* | 1/2010 | Hampton ............ A61B 5/0452 600/523 |
| 2010/0234700 A1* | 9/2010 | Bowers ............ A61B 5/0006 600/301 |
| 2010/0249860 A1* | 9/2010 | Shuros ............ A61N 1/3625 607/4 |
| 2011/0125040 A1 | 5/2011 | Crawford et al. |
| 2014/0222095 A1 | 8/2014 | Einy |
| 2015/0217121 A1* | 8/2015 | Subramanian ....... A61N 1/3968 607/4 |

FOREIGN PATENT DOCUMENTS

| | | |
|---|---|---|
| KR | 1251081 | 3/2013 |
| KR | 20140126649 A | 10/2014 |

\* cited by examiner

CONTROLLER, AND PATCH TYPE AUTOMATED EXTERNAL DEFIBRILLATOR FOR CONTROLLING DEFIBRILLATION USING THE SAME

PRIORITY STATEMENT

This application claims priority under 35 U.S.C. §119(a) from Korean Patent Application No. 10-2015-0064783 filed on May 8, 2015, the disclosure of which is hereby incorporated by reference in its entirety.

BACKGROUND

The present inventive concept relates to defibrillators. In particular, the inventive concept relates to automated external defibrillators.

An automated external defibrillator (AED) is a portable electronic device which automatically diagnoses cardiac arrhythmias threatening a life such as ventricular fibrillation and ventricular tachycardia of a patient, and cures the cardiac arrhythmias through defibrillation. The AED stops arrhythmia and allows a heart to rebuild an effective rhythm.

An AED is a portable electronic device, but a patient having cardiac arrhythmias cannot carry the AED all the time. Moreover, even if an AED happens to be stored in a public area in which a person has cardiac arrhythmias and falls to the ground, for example, signaling that even to surrounding persons, the AED can not be used to provide appropriate first aid to if the surrounding persons do not know how to use the AED properly.

And, even if a surrounding person locates the AED and knows how to use the AED correctly, that person needs to attach pads of the AED correctly to the patient's chest, after which the AED analyzes an electrocardiogram of the patient and audibly instructs the person coming to the patient's aid to provide an electrical shock to the patient in a manner as a result of the analysis. Then such an electrical shock is provided to the patient only once the surrounding person presses a designated button of the AED. A lot of time elapses as these procedures are performed. As the time elapses, the survival rate of a patient decreases considerably.

SUMMARY

One example of a wearable patch-type automated external defibrillator (AED), according to the present inventive concept, includes a battery having a capacity to store electrical energy for defibrillation, a controller operatively electrically connected to the battery, and configured to control a discharging of the battery, and electrodes operatively electrically connected to the battery and the controller. The battery, controller and the electrodes are integral and collectively constitute a skin patch sized and shaped to be worn by a patient on a region of the patient adjacent the heart of the patient. At least some of the electrodes are disposed in the skin patch at locations at which the at least some of the electrodes up electrical activity of the heart when the skin patch is worn on the region of the patient adjacent the heart of the patient, and these electrodes transmit ECG signals representative of the electrical activity of the heart of the patient wearing the AED. Also, the controller is configured to automatically provide electrical energy stored in the battery to at least one of the electrodes in a defibrillation mode. The defibrillation mode is triggered when an analysis of ECG signals received through the at least one electrode indicates the patient wearing the AED requires defibrillation.

One example of a controller, according to the present inventive concept, includes an ECG sensor chip which generates ECG output signals using a difference between a first ECG signal output from a first electrocardiogram (ECG) electrode and a second ECG signal output from a second ECG electrode, an analog-to-digital converter which converts the ECG output signals into ECG digital signals, a CPU which analyzes a heart rhythm of a patient using the ECG digital signals and generates a control signal based on a result of the analysis, a wireless circuit which converts data output from the CPU and related to the heart rhythm into wireless data, and a defibrillator circuit which automatically connects terminals of the battery and defibrillation electrodes to provide the patient with a shock in response to the control signal.

Another example of a wearable patch-type AED, according to the present inventive concept, includes a first AED pad, and a controller and in which the first AED pad includes a first battery having a capacity to store electrical energy for defibrillation of a patient who wears the AED, a first electrocardiogram (ECG) electrode, and a first defibrillation electrode, in which the controller is operatively connected to the first ECG electrode, the first defibrillation electrode and the first battery, and in which the controller includes an ECG sensor chip configured to generate ECG output signals based on a first signal output from the first ECG electrode, an analog-to-digital converter operatively connected to the ECG sensor chip to receive the ECG output signal from the ECG sensor chip and convert the ECG output signals into ECG digital signals, a CPU operatively connected to the analog-to-digital converter to receive the ECG output signals therefrom, a wireless circuit operatively connected to the CPU, and a defibrillator circuit. The CPU is configured to analyze the ECG digital signals and generate, as a result of the analysis, data representative of a heart rhythm of the patient. The data includes a control signal when an abnormality in the heart rhythm is detected from the analysis of the ECG digital signals. The wireless circuit is operatively connected to the CPU to receive the data generated by the CPU and configured to convert the data received from the CPU into wireless data. The defibrillator circuit is configured to automatically electrically connect the first battery and the first defibrillation electrode in response to the control signal such that the first battery provides the patient with a shock through the first defibrillation electrode.

An example of an external defibrillator, according to the present inventive concept, also includes first and second pads configured for attachment to a skin of a patient at regions, respectively, near the heart of the patient, and cable running between the first and second pads. The second pad includes a battery having a capacity to store electrical energy for defibrillation. The first pad includes a controller operatively electrically connected to the battery via the cable, and configured to control a discharging of the battery. Furthermore, the first pad includes an electrode operatively connected to the controller to transmit first ECG signals to the controller representative of electrical activity of the heart. The second pad includes an electrode electrically connected to the controller via the cable to transmit second ECG signals to the controller representative of electrical activity of the heart. Also, the first pad includes an electrode operatively connected to the battery, and the second pad includes an electrode operatively connected to the battery. The controller is configured to automatically provide, in a defibrillation mode, electrical energy stored in the battery to the electrodes of the first and second pads that are operatively connected to the battery. The defibrillation mode is triggered when an analysis of ECG signals received by the controller indicates the patient wearing the skin patch requires defibrillation.

BRIEF DESCRIPTION OF THE DRAWINGS

These and/or other aspects and advantages of the present general inventive concept will become apparent and more readily appreciated from the following description of examples thereof, taken in conjunction with the accompanying drawings of which.

DETAILED DESCRIPTION

Figure 1:
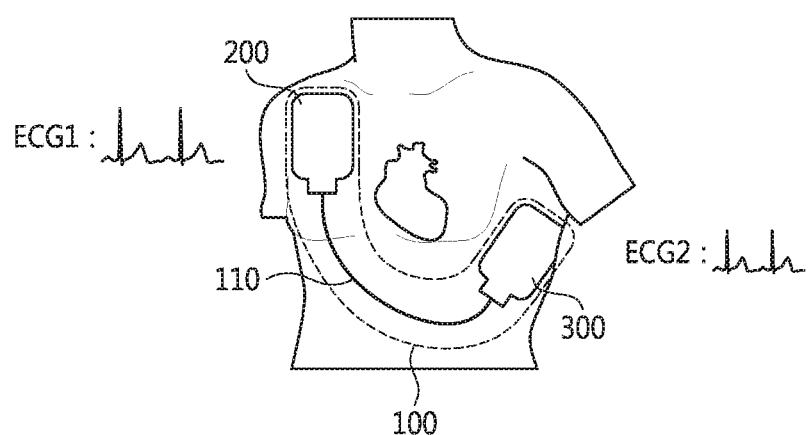
FIG. 1 is a conceptual diagram of a wearable patch-type automated external defibrillator (AED) according to the present inventive concept as attached to a patient.

The present inventive concept now will be described more fully hereinafter with reference to the accompanying drawings, in which examples of the inventive concept are shown. This inventive concept may, however, be realized in many different forms and should not be construed as limited to the examples set forth herein. Rather, these examples are provided so that this disclosure will be thorough and complete, and will fully convey the scope of the inventive concept to those skilled in the art. In the drawings, the size and relative sizes of components and regions may be exaggerated for clarity. Like numbers designate like elements throughout the drawings.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. As used herein, the term "and/or" includes any and all combinations of one or more of the associated listed items and may be abbreviated as "/".

It will be understood that, although the terms first, second, etc. may be used herein to describe various elements, these elements should not be limited by these terms. These terms are only used to distinguish one element from another. For example, a first signal could be termed a second signal, and, similarly, a second signal could be termed a first signal without departing from the teachings of the disclosure.

The terminology used herein is for the purpose of describing particular examples only and is not intended to be limiting. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and/or the present application, and will not be interpreted in an idealized or overly formal sense unless expressly so defined herein. For example, the term "patient" as used in this specification will refer to any person wearing an AED according to the inventive concept regardless of whether the person is actively under the care of any particular medical personnel and, in the case in which the person is under medical care, irrespective of the type of provider of that care unless otherwise specified. The term "pad" will thus be understood as referring to a relatively flat and at least somewhat flexible member having a soft covering or film and which may include a component(s) comprising or being integral with such a covering or membrane. The term "patch" as used in this specification will thus refer to any material(s), e.g., covering or film, permanent or disposable, having a surface by which active (electrical) components of the AED are attached to the skin of the patient. The term "skin patch" as used in this specification will thus refer to a patch that may be adhered to the skin of a patient and is this sized and shaped to cover a particular region(s) of the skin of a typical person.

FIG. 1 shows an example of a wearable patch-type automated external defibrillator (AED) according to the present inventive concept, as attached to an end user (referred to hereinafter as "a patient"). Referring to FIG. 1, the wearable patch-type AED 100 may include a first AED pad 200 which includes a relatively soft covering or membrane (referred to hereinafter simply as a cover) and at least one electrode embedded or disposed in or otherwise integrated with the cover), a second AED pad 300 which includes a cover and at least one electrode embedded or disposed in or otherwise integrated with the cover, and a cable 110 which connects the first AED pad 200 and the second AED pad 300. The cable 110 may be attached to and detached from the first AED pad 200 and the second AED pad 300. The cable 110 includes one or more wires.

Figure 2:
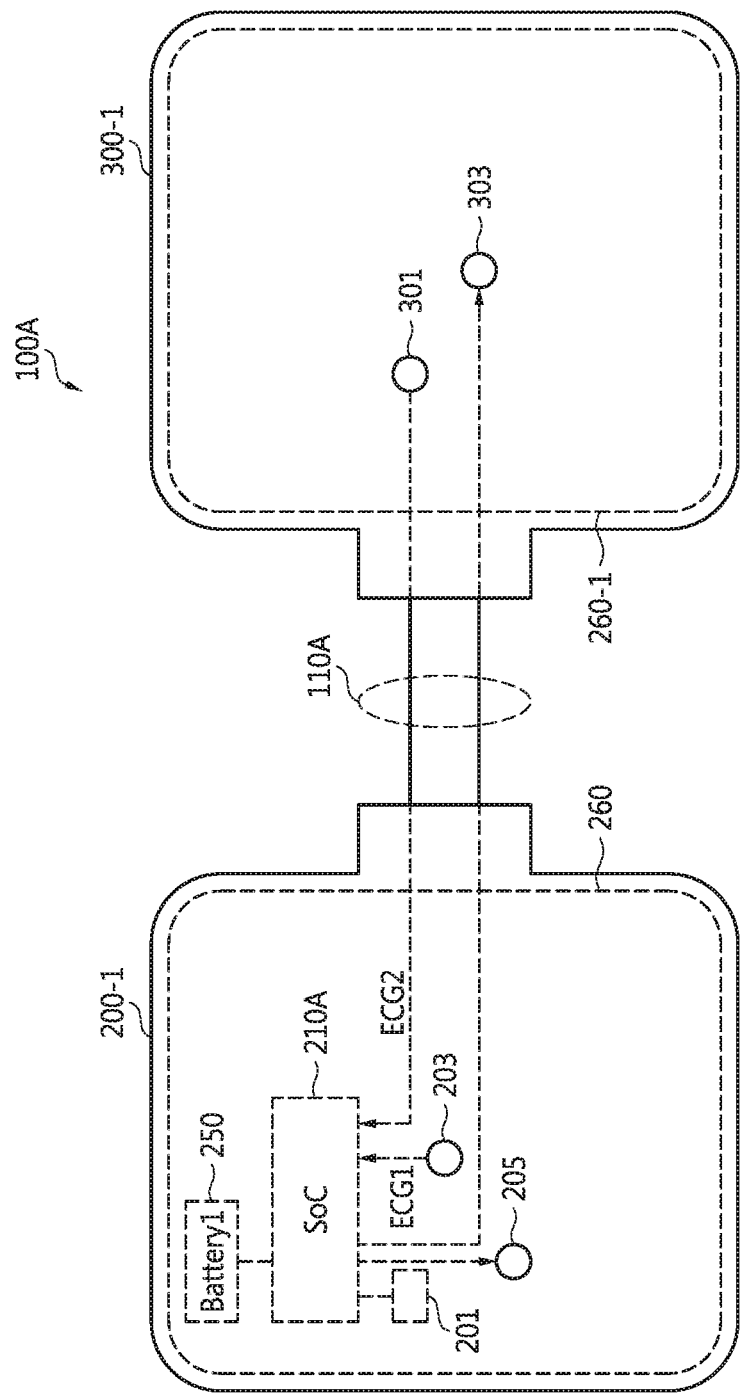
FIG. 2 is a schematic diagram of an example of the wearable patch-type AED shown in FIG. 1.

The covers of the first AED pad 200 and the second AED pad 300 may be contiguous with one another as shown by the chained lines in the figure and may envelop and electrically insulate the wiring of the cable 110A, or the covers may be discrete as shown by the solid lines in FIG. 2. In any case, the covers of the AED pads may collectively constitute a patch by which the AED can be adhered to the patient's skin.

In the illustrated example, the first AED pad 200 is dedicated to be attached to the right side of a patient's chest just above the nipple and the second AED pad 300 is dedicated to be attached to the left side of the ribcage of the patient slightly below the other nipple. ECG1 and ECG2 designate electrocardiogram (ECG) signals, respectively, which may be produced by the AED pads 200 and 300, respectively. The ECG1 and ECG2 signals have different waveforms because the AED pads 200 and 300 are located different distances from the heart.

That is, at least one electrode of the first AED pad 200 may detect electrical activity of the heart and transmit the activity as a first electrocardiogram signal ECG1 to a processing circuit of the AED, and at least one electrode of the second AED pad 300 may also detect the electrical activity the heart and transit the activity as a second electrocardiogram signal ECG2 to the processing circuit of the AED.

According to one example, the processing circuit may be embedded in the membrane of the first AED pad 200, i.e., may be part of the first AED pad 200. Alternatively, the processing circuit may embedded in the membrane of, i.e., may be part of, the second AED pad 300. In still another example, one portion of the processing circuit may form part of the first AED pad 200, and the other portion of the processing circuit may form the second AED pad 300.

The wearable patch-type AED 100, unlike a conventional AED, may always be attached to a patient at the periphery of the patient's heart (that is, until the patient removes the wearable patch-type AED 100), and analyze electrocardiogram signals of the patient in real time. As will be described in more detail below, the patch-type AED 100 may also include a battery embedded or otherwise disposed in one of the membranes of the AED 100 for automatically providing the patient with an electrical shock (or electrical energy) instantly when the patient requires defibrillation as a result of the real-time analysis of the electrocardiogram signals.

FIG. 2 is a block diagram which shows in more detail an example of the patch-type AED shown in FIG. 1. Referring to FIGS. 1 and 2, a wearable patch-type AED 100A according to the inventive concept may include a first AED pad 200-1, a second AED pad 300-1, and a cable 110A which connects the first AED pad 200-1 and the second AED pad 300-1.

The first AED pad 200-1 of this example includes a processing circuit, e.g., a controller 210A, a first battery 250 and a second battery 260, a first ECG electrode 203, and a first defibrillation electrode 205. The first AED pad 200-1 may further include a ground electrode 201. The controller 210A may be a system on chip (SoC). In other examples, the controller is a chip set, or a plurality of chips.

For example, the first battery 250 may provide the controller 210A with an operation voltage, and the second battery 260 may provide a patient with a defibrillation voltage (or an electrical shock or electrical energy) for defibrillation. Although FIG. 2 shows the first battery 250 and second battery 260 as separate components, i.e., as discrete batteries, the first battery 250 and the second battery 260 may be integrated as a single battery. Furthermore, although FIG. 2 shows each of the first battery 250 and the second battery 260 in the form of a rectangle, sizes and shapes of the first battery 250 and the second battery 260 of the first AED pad 200-1 are not limited. Also, although FIG. 2 shows the ground electrode 201 as part of the first AED pad 200-1, the ground electrode 201 may instead be part of the second AED pad 300-1.

According to one example, the second battery 260 is part of the first AED pad 200-1 and a third battery 260-1 is part of the second AED pad 300-1 so as to maximize the capacity or energy for defibrillation. In this example, the second battery 260 and the third battery 260-1 may be connected to each other in series through the cable 110A. According to still another example, the second battery 260 may itself be part of the second AED pad 300-1.

Furthermore, each of the batteries 260 and 260-1 may be a flexible battery. Also, each of the batteries 250, 260, and 260-1 may be a rechargeable battery. An additional battery may be attached to or detached from each of the batteries 260 and 260-1 so as to increase capacity or energy of each of the batteries 260 and 260-1. For example, each additional battery may be connectable to each of the batteries 260 and 260-1 in series.

Each of the batteries 250, 260, and 260-1 which can be embedded or otherwise disposed in (or attached externally to) a membrane of the wearable patch-type AED 100A may be a wireless charging battery or a wireless rechargeable battery. In particular, each of the batteries 250, 260, and 260-1 may be charged through an inductive charging technology or a wireless charging technology. In these cases, the defibrillator circuit 235 may control wireless charging of each of the batteries 250, 260, and 260-1.

The first ECG electrode 203 and the first defibrillation electrode 205 may protrude from an attachment surface (or a bottom surface) of the membrane of the first AED pad 200-1. Thus, when a patient wears the first AED pad 200-1, the protruding first ECG electrode 203 and the protruding first defibrillation electrode 205 may contact the skin of the patient. Such skin contact may be effective in the acquisition of the first ECG signal ECG1 by the first AED pad 200-1 and in the provision of a defibrillation voltage by the first defibrillation electrode 205.

Alternatively, the wearable patch-type AED 100A may include a medium covering and attached to at least one of the protruding first ECG electrode 203 and the first defibrillation electrode 205 so as to be interposed between the patient's skin and the first ECG electrode 203 and/or the first defibrillation electrode 205. For example, the medium may be a disposable film or a disposable gel discarded after use, but is not limited thereto. The medium may be material selected for its ability to minimize impedance caused by contact between a patient and at least one of the first ECG electrode 203 and the first defibrillation electrode 205.

That is, the wearable patch-type AED 100A may be realized as a dry-type wearable patch-type AED for direct connection between the skin and electrode(s) or as a wet-type wearable patch-type AED for an indirect connection between the skin and electrode(s). In the case of the latter, the medium by which the AED is directly attached to the skin of the end user may constitute the skin patch of the AED.

The second AED pad 300-1 may include a second ECG electrode 301 and a second defibrillation electrode 303. As described above, the third battery 260-1 for defibrillation may be additionally provided as part of the second AED pad 300-1. The third battery 260-1 may be a chargeable flexible battery, and the third battery 260-1 may be charged in a wired or wireless manner.

Moreover, the second battery 260 and/or the third battery 260-1 may be slightly smaller than the bodies of the AED pad 200-1 and/or AED pad 300-1 in terms of their footprints (surface areas), but the inventive concept is not limited thereto.

The first ECG electrode 203 may transmit the first ECG signal ECG1 to the controller 210A, and the second ECG electrode 301 may transmit the second ECG signal ECG2 to the controller 210A through the cable 110A. For example, the first ECG electrode 203 may be a positive electrode, and the second ECG electrode 301 may be a negative electrode; however, the inventive concept is not limited thereto. The second battery 260 and/or the third battery 260-1 may provide the defibrillation electrodes 205 and 303 with voltages (or energy) for defibrillation under the control of the controller 210A. Accordingly, the cable 110A may include a first wire for transmitting the second ECG signal ECG2 and a second wire for transmitting a defibrillation voltage. For example, the first defibrillation electrode 205 may be a positive electrode and the second defibrillation electrode 303 may be a negative electrode; however, the inventive concept is not limited thereto.

Figure 3:
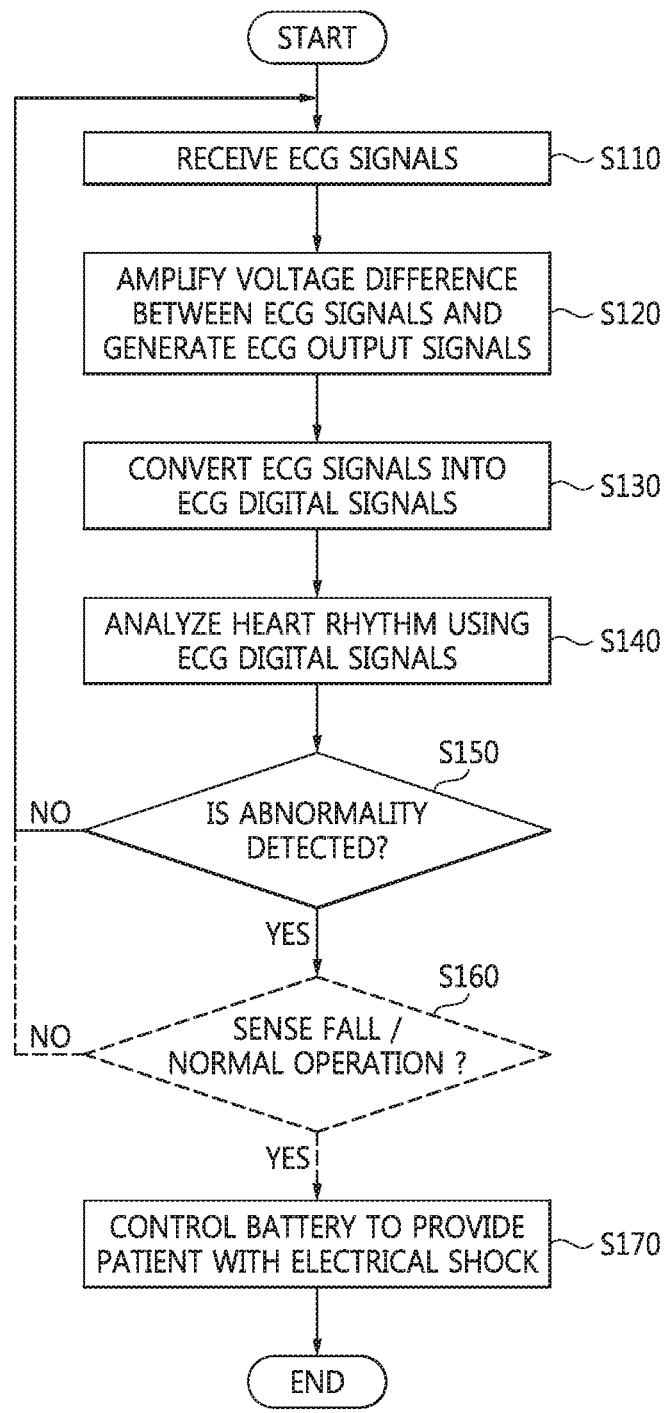
FIG. 3 is a flowchart of an operation of the wearable patch-type AED shown in FIG. 2.
Figure 4:
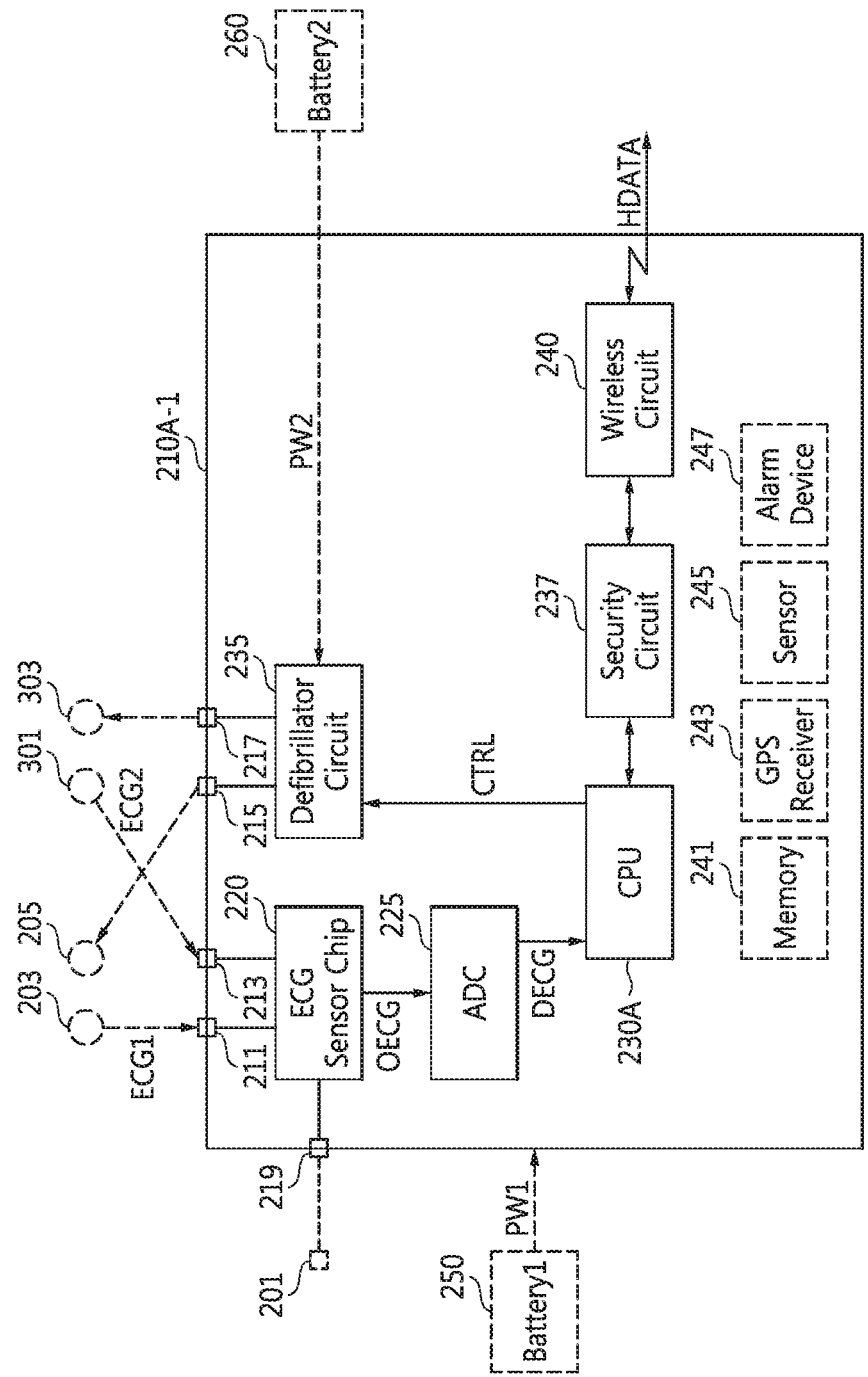
FIG. 4 is a block diagram which shows an example of a controller of the wearable patch-type AED shown in FIG. 2.

FIG. 3 is a flowchart which illustrates an operation of the wearable path-type AED shown in FIG. 2, and FIG. 4 is a block diagram which shows an example 210A-1 of the controller 210A of the wearable path-type AED shown in FIG. 2.

Referring to FIG. 4, a controller 210A-1 may include conductive terminals 211, 213, 215, 217, and 219, an ECG sensor chip 220, an analog-to-digital converter (ADC) 225, a central processing unit (CPU) 230A, a defibrillator circuit 235, a security circuit 237, and a wireless circuit 240. The controller 210A-1 may also include at least one of a memory 241, a GPS receiver 243, a sensor 245, and an alarm 247.

Each of the conductive terminals 211, 213, 215, 217, and 219 may be connected to a corresponding electrode 203, 301, 205, 303, or 201 through a corresponding transmission line. The terminals may be pads (lands of conductive material as shown), pins, bumps, or solder balls. However, the inventive concept is not limited to any particular type of conductive terminals. For purposes of ease of description only, an example in which the conductive terminals 211, 213, 215, 217, and 219 are pads will be described.

Referring to FIGS. 1 to 4, the ECG sensor chip 220 may receive a first ECG signal ECG1 output from the first ECG electrode 203 through a pad 211 and receive a second ECG signal ECG2 output from the second ECG electrode 301 through a pad 213 (S110). The ECG sensor chip 220 may amplify a voltage difference between the first ECG signal ECG1 and the second ECG signal ECG2, and generate an ECG output OECG corresponding to a result of the amplification (S120). Here, the ECG output OECG may be one or more discrete output signals.

The ADC 225 may convert the ECG output OECG into an ECG digital signal DECG and output the ECG digital signal DECG to the CPU 230A (S130). The CPU 230A may analyze a heart rhythm of a patient using the ECG digital signal DECG, generate a control signal CTRL according to a result of the analysis, and output the control signal CTRL to the defibrillator circuit 235 (S140).

The CPU 230A may detect, predict, or analyze sudden cardiac arrest (SCA) of a patient using the ECG digital signal DECG. For example, the CPU 230A may detect, predict, or analyze cardiac arrhythmias such as ventricular fibrillation and/or ventricular Tachycardia using the ECG digital signal DECG (S140).

When an abnormality is not detected in the wearer's heart rhythm (NO in S150), the ECG sensor chip 220 may continue amplifying a voltage difference between ECG signals of a patient (S110).

However, when an abnormality occurs in the heart rhythm (YES in S150), e.g., when cardiac arrhythmias are detected, predicted, or analyzed, the CPU 230A may output a control signal CTRL for controlling defibrillation to the defibrillator circuit 235. Accordingly, the defibrillator circuit 235 may control the second battery 260 so as to provide a patient with an electrical shock (S170). The defibrillator circuit 235 may control charging and discharging of the second battery 260.

The second battery 260 may automatically supply voltages for defibrillation (for example, electrical energy or electrical shock: PW2) to the defibrillation electrodes 205 and 303 through the pads 215 and 217 under the control of the defibrillator circuit 235. For example, the defibrillator circuit 235 may connect a first terminal (for example, a positive terminal) of the second battery 260 and the first defibrillation electrode 205, and connect a second terminal (for example, a negative terminal) of the second battery 260 and the second defibrillation electrode 303. That is, the electrical energy PW2 stored in the second battery 260 may be supplied to a patient through the defibrillation electrodes 205 and 303.

According to one example, the controller 210A-1 is provided with a sensor 245 in the form of a fall sensor which can detect when a patient to which the wearable patch type AED 100 or 100A is attached falls (YES in S160). In this case, the sensor 245 outputs an activated detection signal (S160). Accordingly, the CPU 230A outputs an activated control signal CTRL to the defibrillator circuit 235 when an abnormality occurs in a heart rhythm and an activated detection signal is generated (YES in S150 and YES in S160). Accordingly, the defibrillator circuit 235 controls the second battery 260 so as to provide the patient with an electrical shock (S170).

However, when a patient to which the wearable patch-type AED 100 or 100A is attached has not fallen even when an abnormality occurs in his or her heart rhythm (YES in S150 and NO in S160), the CPU 230A outputs an inactivated control signal CTRL to the defibrillator circuit 235. Accordingly, the defibrillator circuit 235 will not operate the second battery 260 to provide the patient with an electrical shock.

According to one example, the CPU 230A is configured to determine based on the ECG digital signal DECG or a sensing signal output from the sensor 245 whether at least one component of the controller 210A-1 (hardware) and/or at least one operation performed by the CPU 230A (e.g., software) has malfunctioned (S160).

The CPU 230A may output an activated control signal CTRL to the defibrillator circuit 235 when an abnormality occurs in a heart rhythm and the controller 210A-1 is operating normally (YES in S150 and YES in S160). Accordingly, the defibrillator circuit 235 may control the second battery 260 so as to provide a patient with an electrical shock (S170).

However, when the controller 210A-1 malfunctions even if an abnormality occurs in a heart rhythm (YES in S150 and NO in S160), the CPU 230A may output an inactivated control signal CTRL to the defibrillator circuit 235. Accordingly, the defibrillator circuit 235 does not operate the second battery 260 to provide a patient with an electrical shock.

Figure 10:
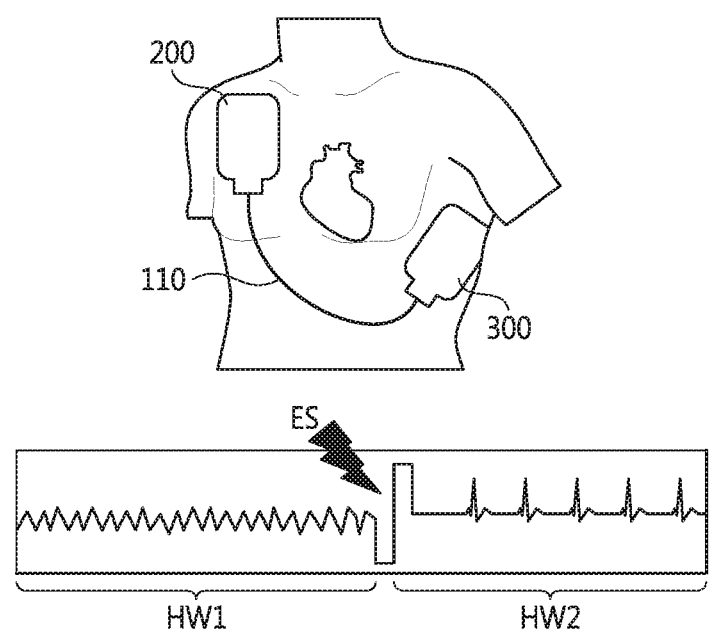
FIG. 10 is a conceptual diagram of a method of performing defibrillation using the wearable patch-type AED shown in FIG. 1 on a patient having sudden cardiac arrest caused by ventricular fibrillation.

FIG. 10 is a conceptual diagram which illustrates a method of automatically performing defibrillation using the wearable patch-type AED 100 shown in FIG. 1 on a patient having sudden cardiac arrest caused by ventricular fibrillation. Referring to FIGS. 3, 4, and 10, when ventricular fibrillation HW1 is detected or predicted by the CPU 230A, the second battery 260 may automatically supply an electrical shock ES to the defibrillation electrodes 205 and 303 through the pads 215 and 217 under the control of the defibrillator circuit 235. Accordingly, a heart rhythm HW2 of a patient may be recovered by defibrillation so as to return to normal.

Figure 11:
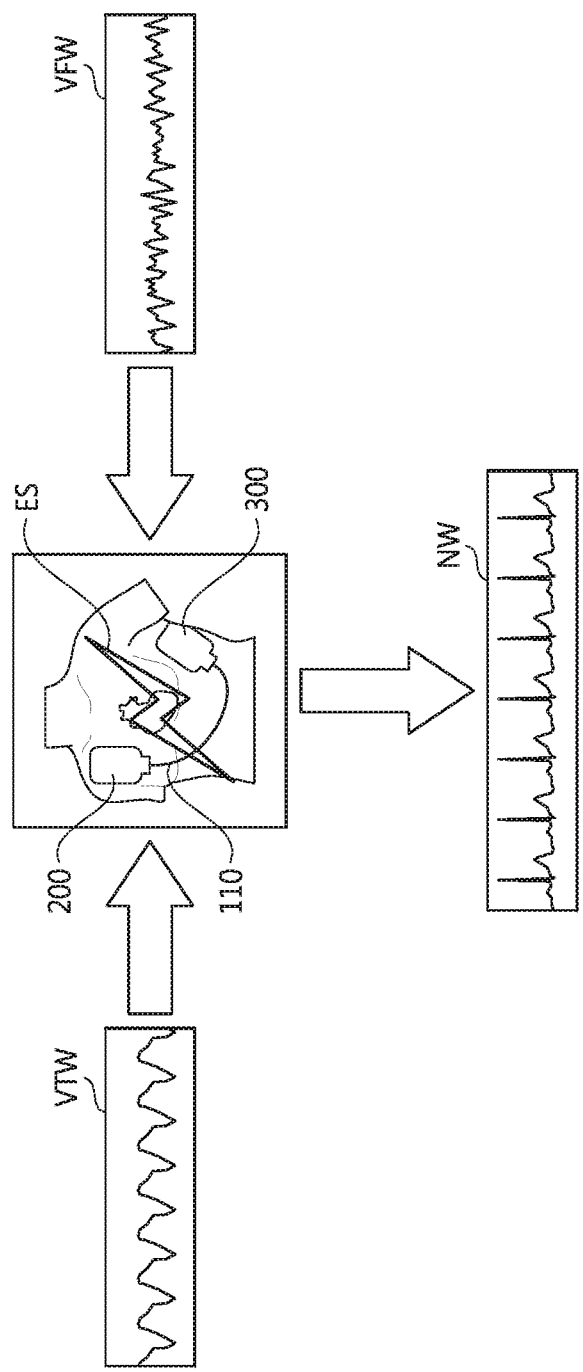
FIG. 11 is a conceptual diagram of a method of performing defibrillation using the wearable patch-type AED shown in FIG. 1 on a patient having sudden cardiac arrest caused by ventricular fibrillation or ventricular Tachycardia.

FIG. 11 is a conceptual diagram which illustrates a method of automatically performing defibrillation using the wearable patch-type AED shown in FIG. 1 on a patient having sudden cardiac arrest caused by ventricular fibrillation or ventricular Tachycardia. Referring to FIGS. 3, 4, 10, and 11, an electrical shock ES supplied to a patient is contrived so that a ventricular Tachycardia waveform VTW and a ventricular fibrillation waveform VFW return to normal as represented by the normal waveform NW.

Ventricular Tachycardia waveform VTW is a waveform generated when ECG signals are generated by a rapid heart beat caused by tachycardia or other improper electrical activity in the heart. Ventricular fibrillation waveform VFW is a waveform generated when ECG signals are generated by uncoordinated contraction of cardiac muscles of the ventricles in a heart.

In any case, abnormal heart activity can be sensed from ECG signals produced by the wearable patch-type AED according to the inventive concept, and based on the ECG signals an electrical shock ES may be designed and applied to a patient automatically by the AED whereupon the signals generated by the activity of the patient's heart have a normal waveform NW. That is, automatic defibrillation as used in the present specification may refer to an operation that arrests cardiac arrhythmias, such as ventricular fibrillation and/or ventricular Tachycardia, using electrical energy (shock) to restore a normal heart rhythm.

The security circuit 237 may encode data output from the CPU 230A and related to a heart rhythm into security data, and output the encoded security data to the wireless circuit 240. Moreover, the security circuit 237 may decode the data transmitted from the wireless circuit 240 and transmit the decoded data to the CPU 230A. For example, the security circuit 237 may be configured, e.g., programmed, with an encryption and decryption code.

The wireless circuit 240 may transmit encoded security data output from the security circuit 237 to an external smart device (e.g., a wireless communication device) under the control of the CPU 230A. The controller 210A-1 may use a communication circuit, e.g., the wireless circuit 240, for a connection to the external smart device. For example, the controller 210A-1 may determine what kind of external smart device the communication circuit is connected to.

The wireless circuit 240 may transmit data related to the ECG signals ECG1 and ECG2, e.g., security data, to the external smart device through a local area network (LAN), a wireless local area network (WLAN) such as wireless fidelity (Wi-Fi), a wireless personal area network (WPAN) such as Bluetooth, a wireless universal serial bus (USB), a Zigbee, a near field communication (NFC), a radio-frequency identification (RFID), or a mobile cellular network. For example, the mobile communication network may be a $3^{rd}$ generation (3G) mobile communication network, a $4^{th}$ generation (4G) mobile communication network, or a long term evolution mobile communication network (LTE$^T$). To these ends, the wireless circuit 240 may include a transceiver and an antenna for modem communication. The Bluetooth interface may support Bluetooth Low Energy (BLE).

The memory 241 may store information on a patient (patient data) and/or data related to the ECG signals ECG1 and ECG2 under the control of the CPU 230A. For example, the data may include an ECG signal, data related to a heart rate, data related to cardiac arrhythmias, data related to ventricular fibrillation (e.g., a history of ventricular fibrillation and a history of defibrillation), positional data generated by the GPS receiver 243, sensing data generated by the sensor 245, and/or data generated by the alarm 247. For example, the data may be encoded or decoded by the security circuit 237.

The memory 241 may store a boot image for booting the wearable patch type AED 100A and an application to be performed by the CPU 230A. For example, the application may be an application for defibrillation described later with reference to FIGS. 5 and 6 or an application for defibrillation described later with reference to FIGS. 12 to 17, but is not limited thereto.

To these ends, the memory 241 may comprise a volatile memory and/or a non-volatile memory. The volatile memory may be a random access memory (RAM), a dynamic RAM (DRAM), or a static RAM (SRAM), but is not limited thereto.

The non-volatile memory may be an electrically erasable programmable read-only memory (EEPROM), a flash memory, a magnetic RAM (MRAM), a spin-transfer torque MRAM, a ferroelectric RAM (FeRAM), a phase change RAM (PRAM), a resistive RAM (RRAM), a holographic memory, a molecular electronics memory device, or an insulator resistance change memory, but is not limited thereto.

The GPS receiver 243 which is used as an example of the positional information generator may generate positional information of a patient and/or positional information of the patient, when sudden cardiac arrest occurs and may transmit the generated positional information to the memory 241 or the wireless circuit 240 all under the control of the CPU 230A. The positional information may be generated when an activated control signal CTRL is generated.

As mentioned above, the sensor 245 may be of a type that can detect when the patient wearing the sensor 245 falls and in that case transmits a detection signal to the CPU 230A. The CPU 230A may control an operation of the GPS receiver 243 based on the detection signal, and transmit positional information generated by the GPS receiver 243 to the memory 241 or the wireless circuit 240. As was also described above, when an abnormality occurs in a heart rhythm and an activated detection signal occurs, the CPU 230A may output an activated control signal CTRL to the defibrillator circuit 235.

The sensor 245 may be an acceleration sensor, i.e., may comprise an accelerometer, which can measure a variation in velocity, or a gyro sensor, to detect a fall of a patient, but is not limited thereto. Although one sensor 245 is shown in FIG. 4, a wearable patch type AED according to the inventive concept may include various types of sensors.

The alarm 247 may output an alarm signal to a patient attached to or wearing the wearable patch type AED 100A under the control of the CPU 230A. For example, the alarm 247 may be a speaker or a vibration motor, but is not limited thereto. The alarm signal may be generated when an activated control signal CTRL is generated.

Figure 5:
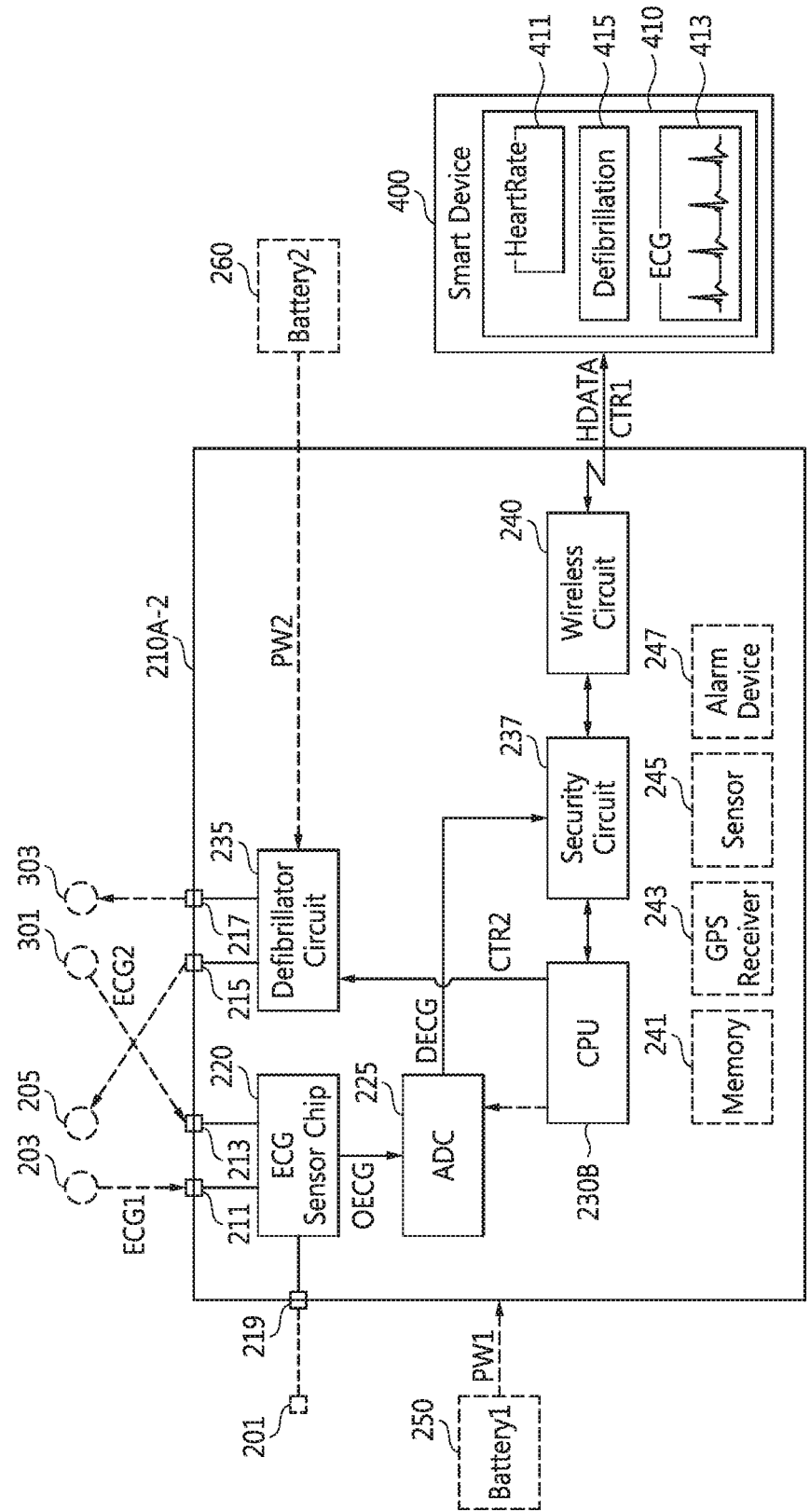
FIG. 5 is a block diagram of a system which includes another example of the controller of the wearable path-type AED shown in FIG. 2 and a smart device.
Figure 6:
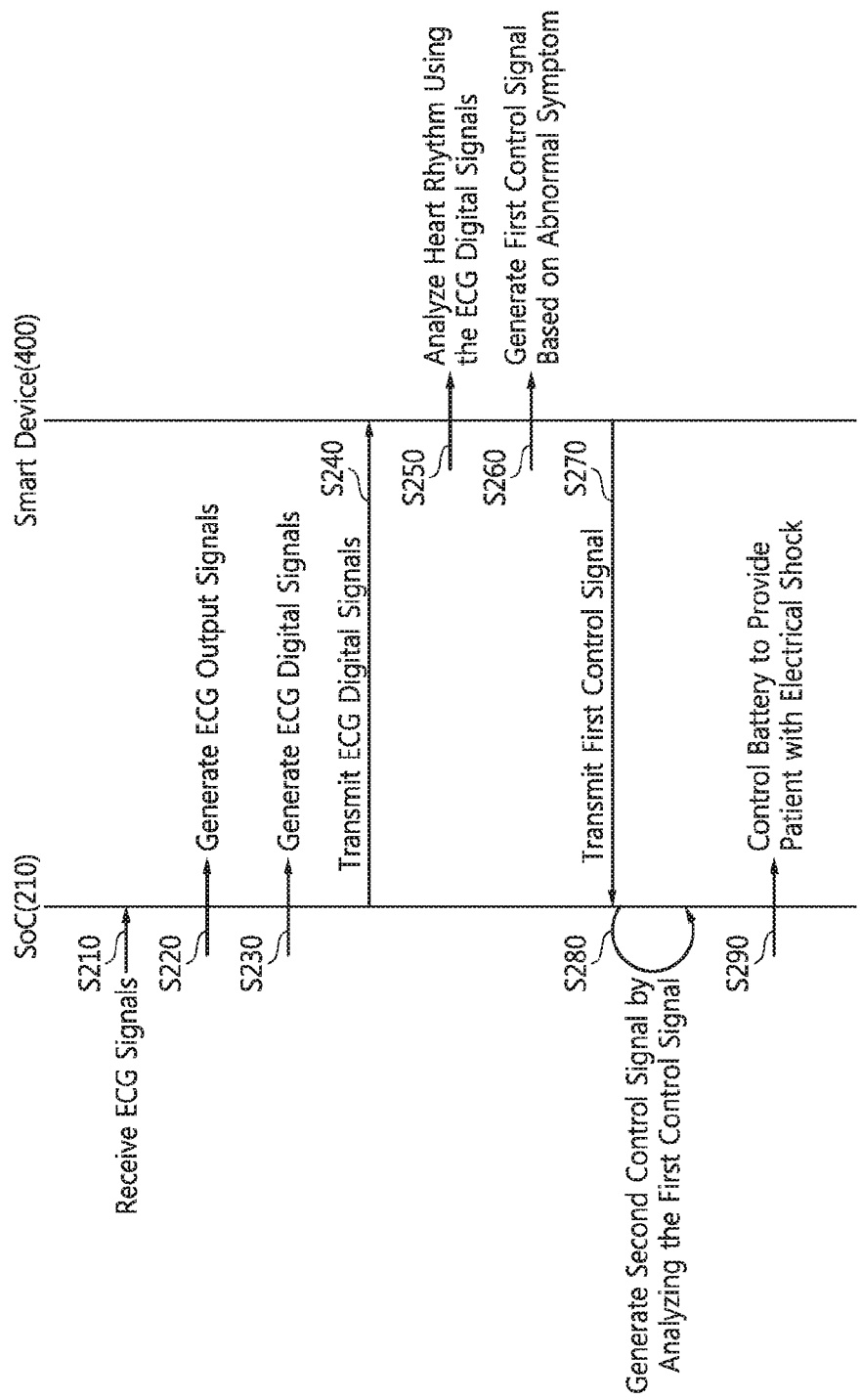
FIG. 6 is a flowchart of a method of performing defibrillation using the system shown in FIG. 5.

FIG. 5 is a block diagram of a system which includes another example 210A-2 of the controller 210A of the wearable path-type AED shown in FIG. 2 and a smart device, and FIG. 6 is a flowchart which illustrates a method of defibrillation using the system shown in FIG. 5.

Referring to FIG. 5, the controller 210A-2 may include the terminals, e.g., pads 211, 213, 215, 217, and 219, the ECG sensor chip 220, the ADC 225, a CPU 230B, the defibrillator circuit 235, the security circuit 237, and the wireless circuit 240. The controller 210A-2 may also include at least one of the memory 241, the GPS receiver 243, the sensor 245, and the alarm 247.

The CPU 230A of the controller 210A-1 shown in FIG. 4 may analyze a heart rhythm of a patient using an ECG digital signal DECG output from the ADC 225, generate a control signal CTRL according to a result of the analysis, and output the control signal CTRL to the defibrillator circuit 235. However, the CPU 230B of the controller 210A-2 of FIG. 5 may control the ADC 225 so that the ECG digital signal DECG output from the ADC 225, e.g., raw data, are transmitted to the security circuit 237.

The ECG sensor chip 220 of FIG. 5 may receive the first ECG signal ECG1 output from the first ECG electrode 203 through the pad 211, and receive the second ECG signal ECG2 output from the second ECG electrode 301 through the pad 213 (S210). The ECG sensor chip 220 may amplify a voltage difference between the first ECG signal ECG1 and the second ECG signal ECG2, and generate an ECG output signal OECG corresponding to a result of the amplification (S220).

The ADC 225 may generate an ECG digital signal DECG from the ECG output signal OECG (S230) and transmit the ECG digital signal DECG to the security circuit 237, and the security circuit 237 may encode the ECG digital signal DECG and output the encoded ECG digital signal to the wireless circuit 240. The wireless circuit 240 may convert the encoded ECG digital signal into wireless ECG signal HDATA and transmit the wireless ECG signal HDATA to the smart device 400 through a wireless communication network (S240). For example, the wireless ECG signal HDATA may include an ECG signal, a signal related to the ECG signal, a signal related to a heart beat, and/or a signal related to cardiac arrhythmias, but is not limited thereto.

The smart device 400 may be a laptop computer, a mobile phone, a smart phone, a tablet PC, a personal digital assistant (PDA), a mobile internet device (MID), a wearable computer, an internet of things (IoT) device, or an internet of everything (IoE) device.

The smart device 400 may include a wired interface and/or a wireless interface, and may be an apparatus which can transmit or receive a command and/or data to or from another apparatus through the wired interface and/or the wireless interface. For example, the smart device 400 may include a communication module configured to communicate with the wireless circuit 240.

Moreover, the smart device 400 may include a communication module (e.g., 1003 of FIG. 18) which can convert a received wireless ECG signal (HDATA) into data usable in the smart device 400, and a CPU which performs an application (e.g., 1002 of FIG. 18) that can analyze the data.

As shown in FIG. 5, an application performed by a CPU of the smart device 400 may analyze a heart rhythm of a patient based on data corresponding to a wireless ECG signal HDATA (S250). For example, the application may display a heart rate 411 and an ECG waveform 413 on a display 410, based on the data.

As a result of analyzing the data, when sudden cardiac arrest of a patient caused by ventricular fibrillation or ventricular tachycardia is predicted, for example, when a particular symptom of a heart problem is detected, an application may display a defibrillation GUI 415 on the display 410. As the defibrillation GUI 415 is touched or pressed by a user of the smart device 400, the application may generate a first control signal CTR1 (S260), and transmit the first control signal CTR1 to the wireless circuit 240 through a communication modem (S270).

According to another example, when a symptom of an abnormal heart function is detected in a of a patient, an application performed by a CPU of the smart device 400 may automatically generate a first control signal CTR1 (S260), and transmit the first control signal CTR1 to the wireless circuit 240 through a communication modem (S260 and S270). The wireless circuit 240 may transmit a control signal related to the first control signal CTR1 to the CPU 230B or the security circuit 237. The security circuit 237 may decode a control signal output from the wireless circuit 240.

The CPU 230B may analyze a control signal output from the wireless circuit 240 or the security circuit 237, generate an activated second control signal CTR2 according to a result of the analysis, and output the activated second control signal CTR2 to the defibrillator circuit 235 (S280). For example, the controller 210A-2 may generate the activated second control signal CTR2 and output the activated second control signal CTR2 to the defibrillator circuit 235 based on the first control signal CTR1 instructing defibrillation (S280).

When a particular symptom of a heart problem is detected, the defibrillator circuit 235 may automatically control discharging of the second battery 260 so as to provide a patient with an electrical shock in response to the activated second control signal CTR2 (S290). The second battery 260 may supply voltages (for example, electrical shock PW2) for defibrillation to the defibrillation electrodes 205 and 303 through the pads 215 and 217 under the control of the defibrillator circuit 235.

As described referring to FIGS. 10 and 11, the wearable patch-type AED 100A including the controller 210A-2 may provide a patient with an electrical shock ES. The electrical shock ES is contrived such that the ECG waveforms produced from the patient as a result of the shock correspond normal waveforms NW.

Figure 7:
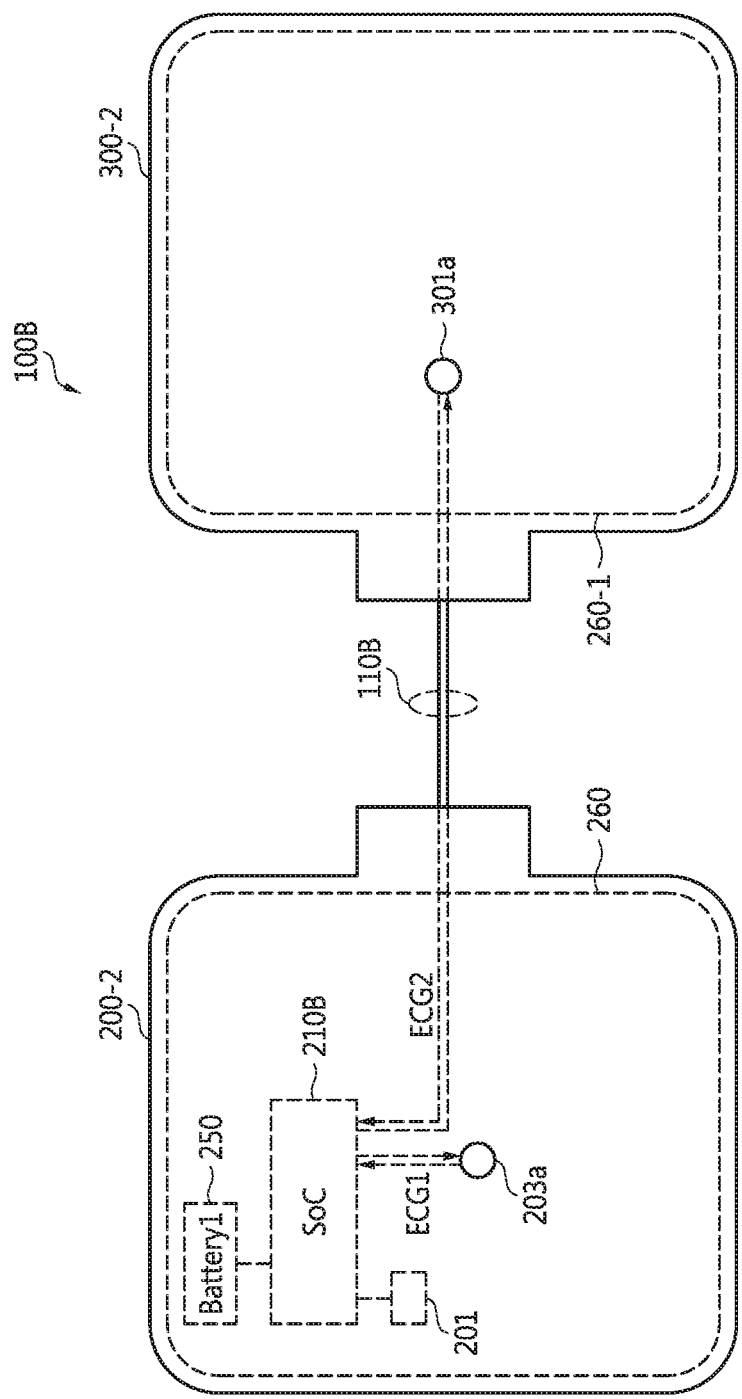
FIG. 7 is a schematic diagram which shows another example of the wearable patch-type AED shown in FIG. 1.

FIG. 7 is a schematic diagram which shows another example of the wearable patch-type AED shown in FIG. 1. Referring to FIG. 7, the wearable patch-type AED 100B may include a first AED pad 200-2 including at least one common electrode 203a, a second AED pad 300-2 including at least one common electrode 301a, and a cable 110B which connects the first AED pad 200-2 and the second AED pad 300-2. The cable 110B may be attached to and detached from the first AED pad 200-2 and the second AED pad 300-2. The cable 110B may include one or more wires.

The common electrode 203a serves as both a first ECG electrode and first defibrillation electrode, and the second common electrode 301a serves as both a second ECG electrode and second defibrillation electrode.

Figure 8:
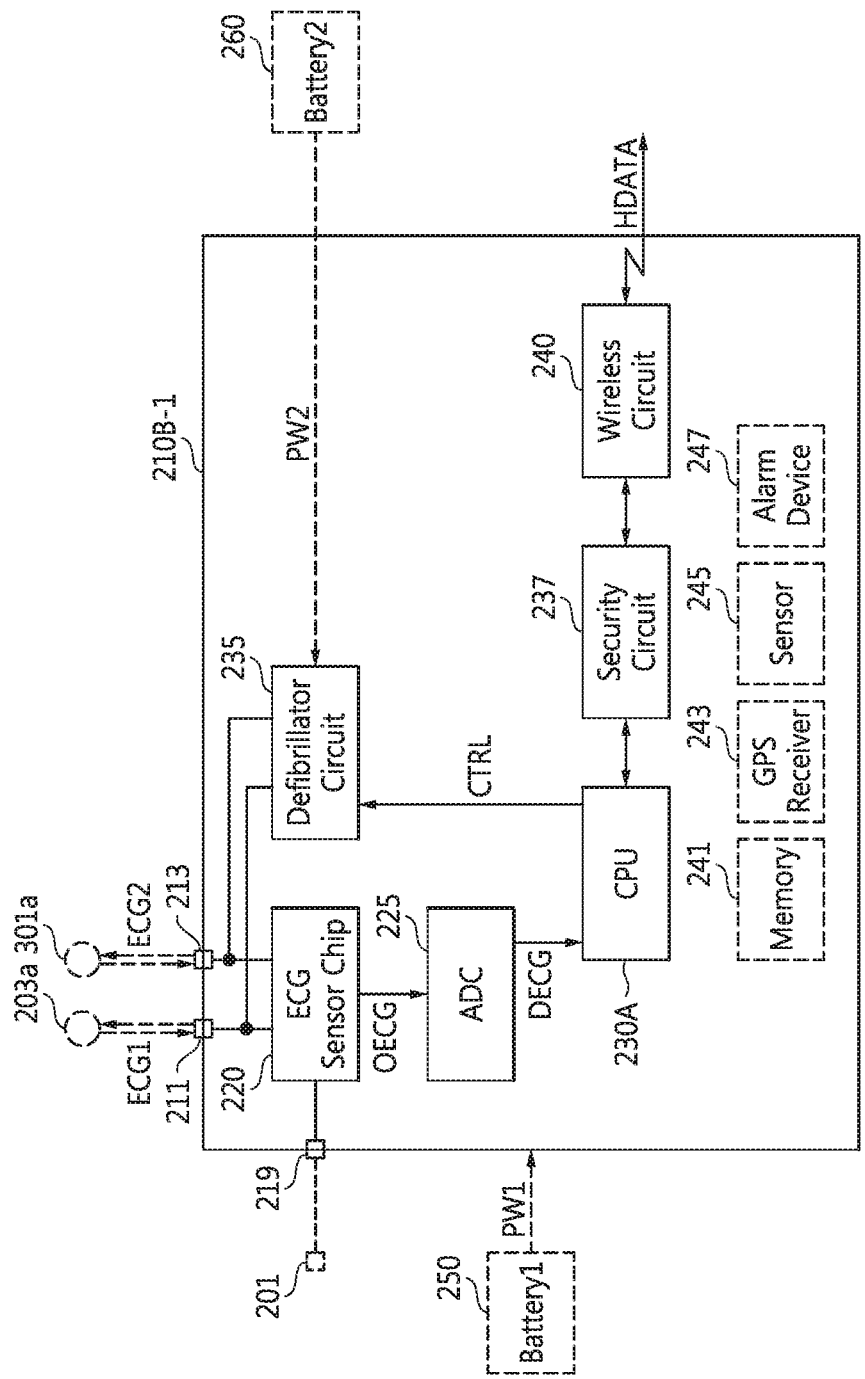
FIG. 8 is a block diagram of an example of a controller of the wearable patch-type AED shown in FIG. 1.

FIG. 8 is a block diagram which shows an example 210B-1 of the controller 210B of the wearable patch-type AED shown in FIGS. 1 and 7. Referring to FIGS. 7 and 8, the controller 210B of FIG. 7 may include the terminals, e.g., pads 211, 213, and 219, the ECG sensor chip 220, the ADC 225, the CPU 230A, the defibrillator circuit 235, the security circuit 237, and the wireless circuit 240. The controller 210B-1 may also include at least one of the memory 241, the GPS receiver 243, the sensor 245, and the alarm 247.

Referring to FIGS. 3, 7, and 8, the ECG sensor chip 220 receives the first ECG signal ECG1 output from the first common electrode 203a through the pad 211, and receives the second ECG signal ECG2 output from the second common electrode 301a through the pad 213 (S110). The ECG sensor chip 220 amplifies a voltage difference between the first ECG signal ECG1 and the second ECG signal ECG2 and generates an ECG output signal OECG corresponding to a result of the amplification (S120).

The ADC 225 converts the ECG output signal OECG into the ECG digital signal DECG, and outputs the ECG digital signal DECG to the CPU 230A (S130). The CPU 230A may analyze a heart rhythm of a patient using the ECG digital signal DECG, generate a control signal CTRL according to a result of the analysis, and output the control signal CTRL to the defibrillator circuit 235 (S140).

For example, the CPU 230A may predict or analyze sudden cardiac arrest of a patient using the ECG digital signal DECG. More specifically, the CPU 230A may predict or analyze ventricular fibrillation of a patient and/or ventricular tachycardia of a patient using the ECG digital signal DECG (S140).

When an abnormality does not occur in a heart rhythm (NO in S150), the ECG sensor chip 220 may perform a step S110 of amplifying a voltage difference between ECG signals of a patient (S110). However, when an abnormality occurs in a heart rhythm (YES in S150), for example, when ventricular fibrillation and/or ventricular tachycardia is detected or predicted, the CPU 230A may output an activated control signal CTRL, which controls defibrillation, to the defibrillator circuit 235. Accordingly, the defibrillator circuit 235 may control discharging of the second battery 260 so as to provide a patient with an electrical shock (S170). The second battery 260 may supply voltages (e.g., electrical shock PW2) for defibrillation to the common electrodes 203a and 301a through the pads 211 and 213 under the control of the defibrillator circuit 235.

According to one example, the sensor 245 is a fall sensor which can detect when a patient wearing the wearable patch-type AED 100 or 100B falls. In the case in which the sensor 245 detects that the patient has fallen (YES in S160), the sensor 245 may output an activated detection signal (S160). Accordingly, the CPU 230A may output an activated control signal CTRL to the defibrillator circuit 235 when an abnormality occurs in a heart rhythm and an activated detection signal is generated (YES in S150 and YES in S160). Accordingly, the defibrillator circuit 235 may control the second battery 260 so as to provide a patient with an electrical shock (S170).

However, when the patient to which an attached wearable patch-type AED 100 or 100B is attached has not fallen, the CPU 230A may output an inactivated control signal CTRL to the defibrillator circuit 235 even though an abnormality in the patient's heart rhythm has been detected (YES in S150 and NO in S160). Accordingly, the defibrillator circuit 235 does not operate (trigger a discharging of) the second battery 260 to provide a patient with an electrical shock.

According to one example, the CPU 230A determines whether at least one hardware component of the controller 210B-1 and/or at least one operation performed by software, for example, has malfunctioned, based on an ECG digital signal DECG or a sensing signal output from the sensor 245 (S160).

The CPU 230A may output an activated control signal CTRL to the defibrillator circuit 235 when an abnormality occurs in a heart rhythm and the controller 210B-1 is operating normally (Yes in S150 and YES in S160). Accordingly, the defibrillator circuit 235 may control the second battery 260 so as to provide a patient with an electrical shock (S170).

However, when the controller 210B-1 malfunctions even in the case of an abnormality occurring in the heart rhythm of the patient (YES in S150 and NO in S160), the CPU 230A may output an inactivated control signal CTRL to the defibrillator circuit 235. In this case, the defibrillator circuit 235 does not trigger the discharging of the second battery 260 of the AED, i.e., the patient is not provided with an electrical shock.

Figure 9:
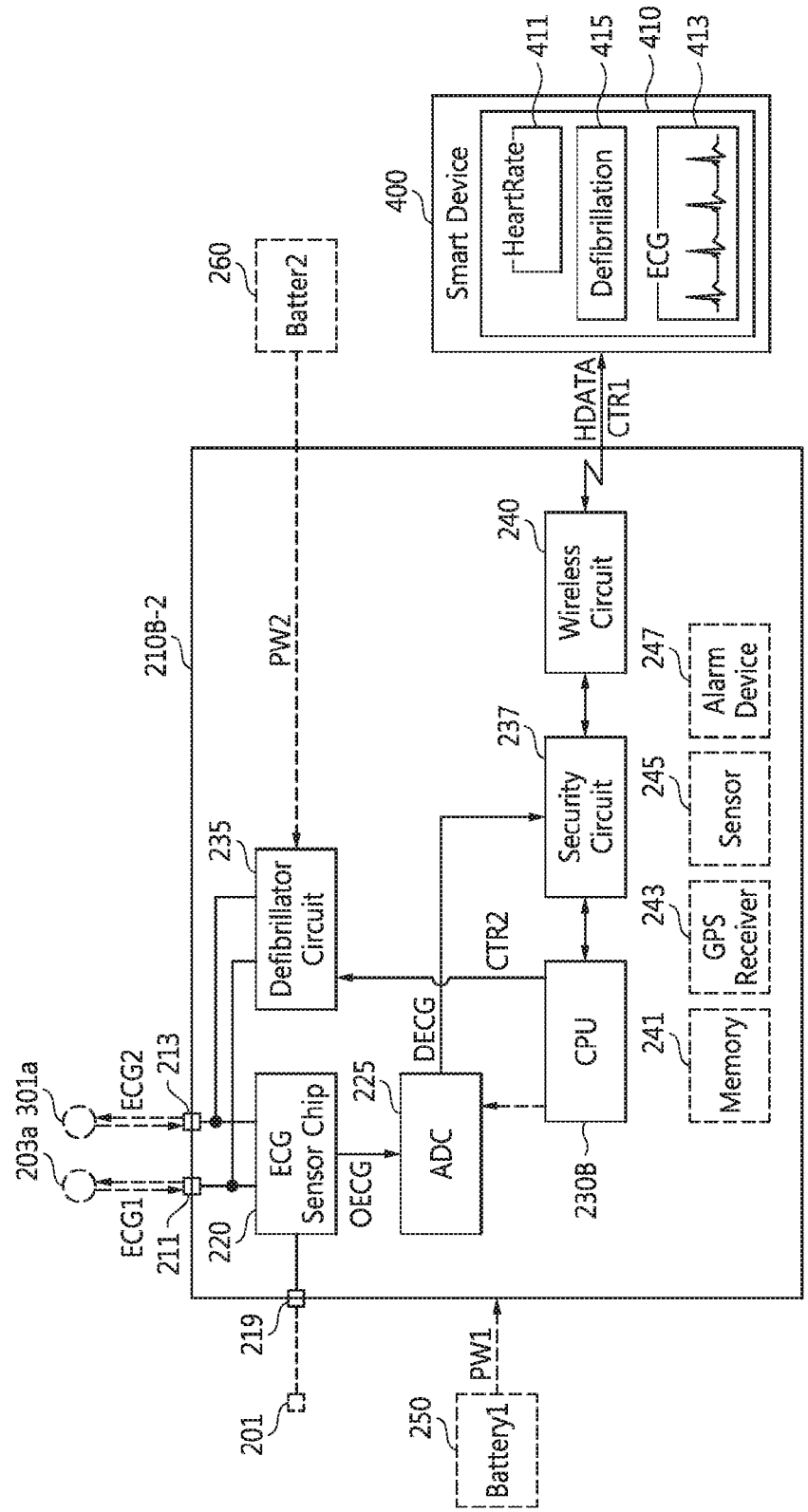
FIG. 9 is a block diagram of a system which includes another example of the controller of the wearable patch-type AED shown in FIG. 7 and a smart device.

FIG. 9 is a block diagram of a system which includes another example 210B-2 of the controller 210B of the wearable patch-type AED shown in FIG. 7 and a smart device. The controller 210B-2 may include the terminals, e.g., the pads 211, 213, and 219, the ECG sensor chip 220, the ADC 22, the CPU 230B, the defibrillator circuit 235, the security circuit 237, and the wireless circuit 240. The controller 210B-2 may further include at least one of the memory 241, the GPS receiver 243, the sensor 245, and the alarm 247.

The CPU 230A of the controller 210B-1 shown in FIG. 8 may analyze a heart rhythm of a patient using an ECG digital signal DECG output from the ADC 225, generate a control signal CTRL according to a result of the analysis, and output the control signal CTRL to the defibrillator circuit 235. On the other hand, the CPU 230B of the controller 210B-2 of FIG. 9 may control the ADC 225 so that the ECG digital signal DECG output from the ADC 225 is transmitted to the security circuit 237.

The ECG sensor chip 220 of FIGS. 6, 7, and 9 receives a first ECG signal ECG1 output from the first common electrode 203a through the pad 211, and receives a second ECG signal ECG2 output from the second common electrode 301a through the pad 213 (S210). The ECG sensor chip 220 amplifies a voltage difference between the first ECG signal ECG1 and the second ECG signal ECG2, and generates an ECG output signal OECG corresponding to a result of the amplification (S220).

The ADC 225 may generate an ECG digital signal DECG from the ECG output signal OECG (S230) and transmit the ECG digital signal DECG to the security circuit 237, and the security circuit 237 may encode the ECG digital signal DECG and output an encoded ECG digital signal to the wireless circuit 240. The wireless circuit 240 may convert the encoded ECG digital signal into a wireless ECG signal (HDADA), and transmit the wireless ECG signal HDATA to the smart device 400 through a wireless communication network (S240). The wireless ECG signal HDATA may include an ECG signal, a signal related to an ECG signal, a signal related to heart beat, and/or a signal related to cardiac arrhythmias, but is not limited thereto.

As shown in FIG. 9, an application of a CPU of the smart device 400 may analyze a heart rhythm of a patient based on data corresponding to the wireless ECG signal HDATA (S250). For example, the application may display the heart rate 411 and the ECG waveform 413 on a display 410 based on the data.

As a result of analyzing the data, when sudden cardiac arrest of a patient caused by ventricular fibrillation or ventricular tachycardia is predicted, for example, when an abnormality is detected in the heart function of a patient, an application may display the defibrillation GUI 415 on the display 410. Once the defibrillation GUI 415 is touched or pressed, the application may generate a first control signal CTR1 (S260), and transmit the first control signal CTR1 to the wireless circuit 240 through a communication modem (S270).

According to another example, when an abnormality is detected in the heart function of a patient, an application performed by a CPU of the smart device 400 may automatically generate a first control signal CTR1 (S260), and transmit the first control signal CTR1 to the wireless circuit 240 through a communication modem (S260 an S270). The wireless circuit 240 may transmit a control signal related to the first control signal CTR1 to the CPU 230 or the security circuit 237.

The CPU 230B may analyze a control signal output from the security circuit 237 or the wireless circuit 240, generate an activated second control signal CTR2 according to a result of the analysis, and output the activated second control signal CTR2 to the defibrillator circuit 235 (S280). For example, the controller 210B-2 may generate the activated second control signal CTR2 and output the activated second control signal CTR2 to the defibrillator circuit 235 based on the first control signal CTR1 instructing defibrillation (S280).

When an abnormality is detected in the heart function of a patient, the defibrillator circuit 235 may automatically control discharging of the second battery 260 so as to provide a patient with an electrical shock in response to the activated second control signal CTR2 (S290). The second battery 260 may supply voltages (e.g., electrical shock PW2) for defibrillation to the common electrodes 203a and 301a through the pads 211 and 213 under the control of the defibrillator circuit 235.

The common electrodes 203a and 301a may be substantially the same as or similar to the ECG electrodes 203 and 301 and/or the defibrillation electrodes 205 and 303 in structure and function. For example, each of the common electrodes 203a and 301a may be a dry-type electrode or a wet-type electrode.

Figure 12:
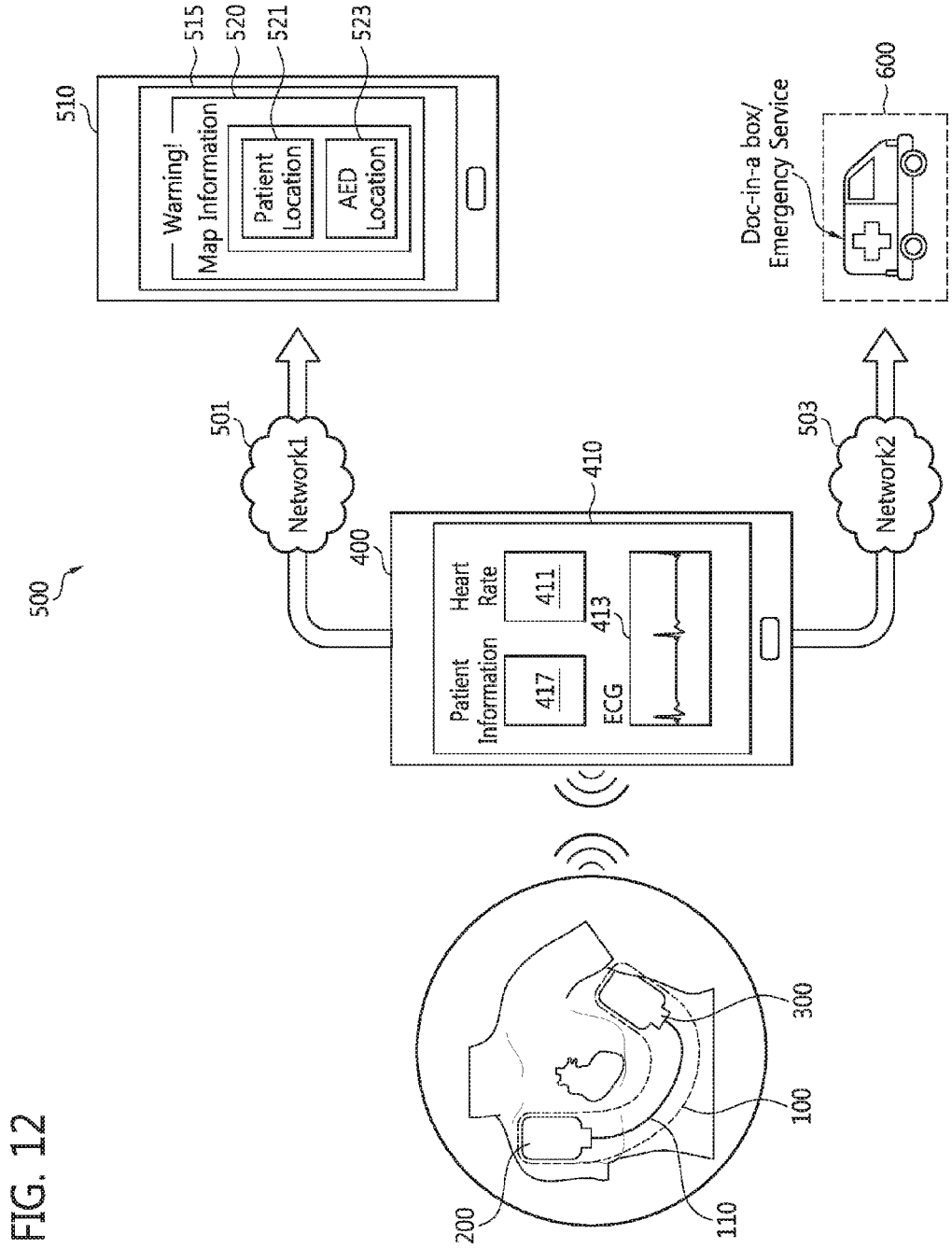
FIG. 12 is a conceptual diagram of an example of a data processing system which includes the wearable patch-type AED shown in FIG. 1.

FIG. 12 is a conceptual diagram of an example of a data processing system which includes the wearable patch-type AED shown in FIG. 1. Referring to FIGS. 1 to 12, a data processing system 500 may include the wearable patch-type AED 100, a first smart device 400, a second smart device 510, and an emergency medical system 600. The wearable patch-type AED 100 may include a first AED pad 200, 200-1, or 200-2 ("200"), a second AED pad 300, 300-1, or 300-2 ("300"), and a cable 110, 110A, or 110B ("110") connected between the first AED pad 200 and the second AED 300.

When a communication module of the first smart device 400 transmits a data transmission request to the wearable patch-type AED 100 through a wireless communication, the wireless circuit 240 of the wearable patch-type AED 100 may transmit the data transmission request to the CPU 230A or 230B.

The CPU 230A or 230B may read data from the memory 241 in response to the data transmission request, and transmit the data read to a communication module of the first smart device 400 through the wireless circuit 240. A first application of a CPU of the first smart device 400 may display at least one of the heart rate 411, the ECG waveform 413, and patient information 417 on the display 410 based on the data.

The communication module of the first smart device 400 may transmit warning data to the second smart device 510 through a network 501 under the control of the first application performed by the CPU of the first smart device 400.

For example, the first application may analyze data transmitted from the wearable patch-type AED 100. When an abnormality is detected in the heart function of a patient according to a result of the analysis, the communication module of the first smart device 400 may generate warning data under the control of the first application and transmit the warning data to the second smart device 510.

For example, the first application may transmit the warning data and positional information of a patient output from the GPS receiver 243 of the wearable patch-type AED 100 or positional information output from a GPS receiver embodied in the first smart device 400 to the communication module. Accordingly, the communication module may transmit the warning data and the positional information to the second smart device 510.

A second application performed by a CPU of the second smart device 510 may display a warning message 520 including map information on a display 515. The map information may include a first map 521 indicating the location of the patient and a second map 523 indicating an AED position.

According to one example, the second map 523 may be generated by the second application, and may be received from the first smart device 400 along with the positional data or the warning data. A user of the second smart device 510 may perform additional defibrillation on a patient using an AED closest to the patient. For example, a user of the second smart device 510 may be a guardian of the patient or a first-aid technician who installed the second application.

The communication module of the first smart device 400 may transmit an emergency signal to the emergency medical system 600 through a network 503 under the control of the first application performed by the CPU of the first smart device 400.

Before defibrillation is automatically performed by the wearable patch-type AED 100, while the defibrillation is performed, or after the defibrillation is performed, the security circuit 237 and/or the wireless circuit 240 of the wearable patch-type AED 100 may transmit data to the first smart device 400 under the control of the CPU 230A or 230B. The first smart device 400 may transmit warning data to the second smart device 510 through a network 501 or transmit an emergency signal to the emergency medical system 600 through the network 503 based on the data or a result of the analysis of the data.

Figure 13:
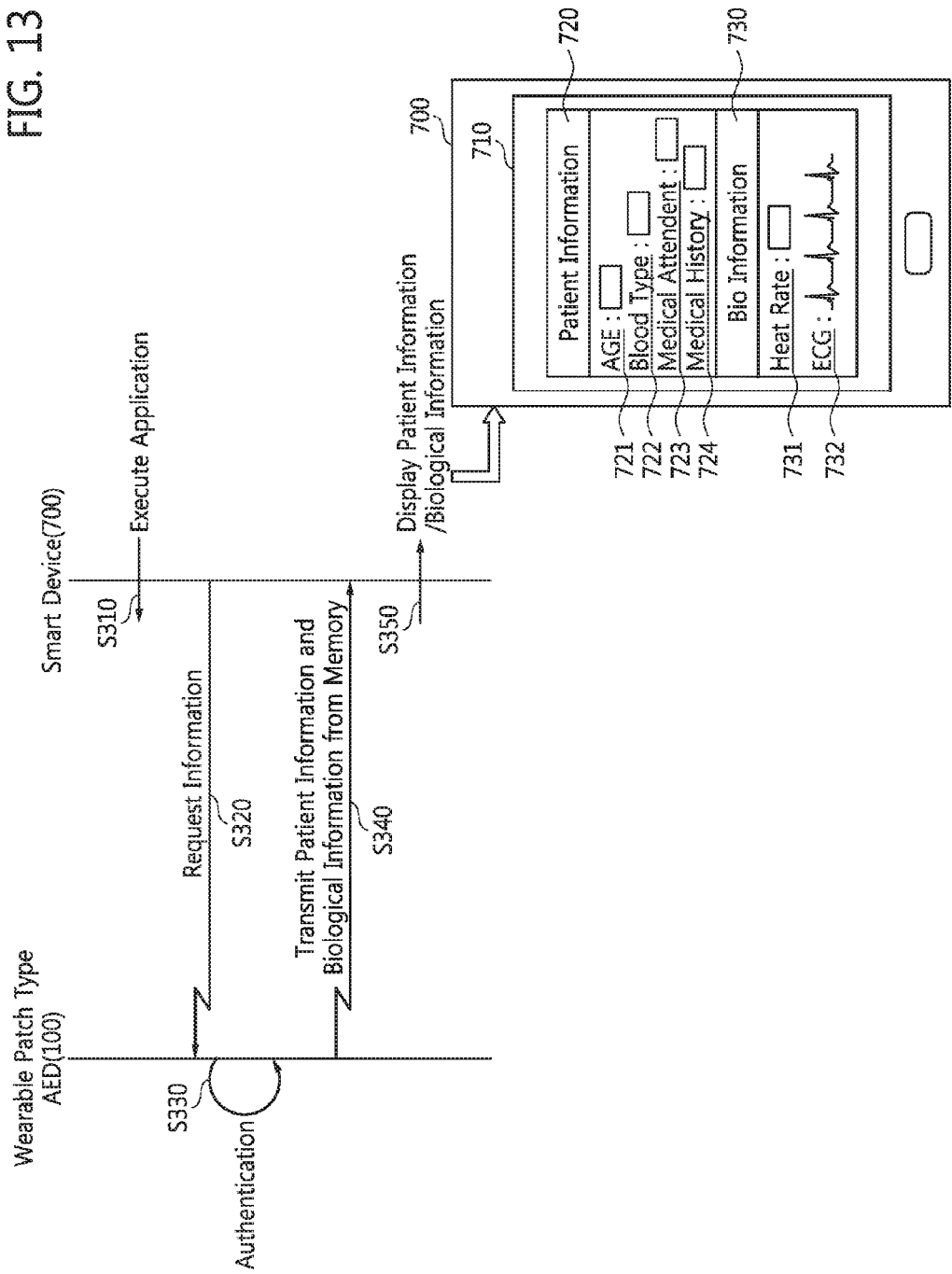
FIG. 13 is a conceptual diagram of another example of a data processing system which includes the wearable patch-type AED shown in FIG. 1.

FIG. 13 is a conceptual diagram of another example of the data processing system which includes the wearable patch-type AED shown in FIG. 1. Referring to FIGS. 1 to 11, and 13, a user of a smart device 700 may execute, i.e., select for use, an application APP installed in the smart device 700 (S310).

A communication module of the smart device 700 may transmit an information request to the wearable patch-type AED 100 under the control of the application APP performed by a CPU of the smart device 700 (S320). A CPU 230A or 230B of the wearable patch-type AED 100 may require authentication by performing an information request through the wireless circuit 240 (S330).

After the authentication is completed, the CPU 230A or 230B may read patient information and biological information from the memory 241, and transmit the patient information and the biological information to the wireless circuit 240 through the security circuit 237. The wireless circuit 240 may transmit the patient information and the biological information to the smart device 700 (S340).

The application APP may display patient information 720 and biological information 730 on a display 710 of the smart device 700 (S350). For example, the patient information 720 may include the age 721, blood type 722, family doctor 723, and a medical history 724 of the patient. The biological information 730 may include heart rate 731 and an ECG waveform 732.

A user of the smart device 700 may determine a state of a patient to which the wearable patch-type AED 100 is attached using the patient information 720 and the biological information 730, and perform a proper medical treatment or emergency diagnostics on the patient according to a result of the determination.

Figure 14:
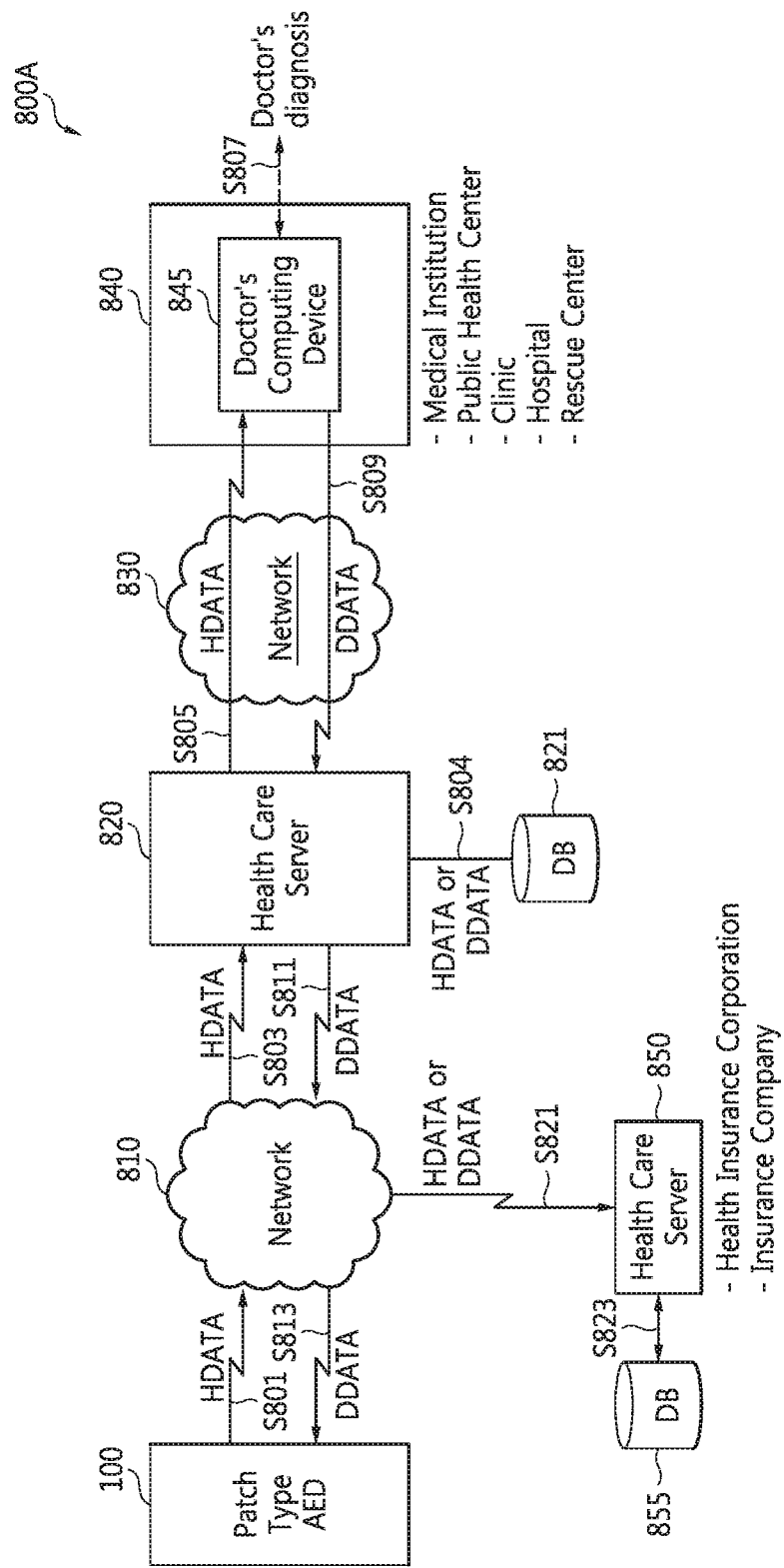
FIGS. 14, 15, 16 and 17 are conceptual diagrams illustrating examples of data processing systems which include the wearable patch-type AED shown in FIG. 1.

FIGS. 14 to 17 are conceptual diagrams of still other examples of data processing systems which include the wearable patch-type AED shown in FIG. 1. Referring to FIG. 14, a data processing system 800A may be used so as to provide a telemedicine service. The data processing system 800A may include the wearable patch-type AED 100 and a first medical server 820 which can communicate with the wearable patch-type AED 100 through a wireless network 810, e.g., the internet or Wi-Fi.

According to one example, the data processing system 800A may further include a second medical server 850 which can communicate with the wearable patch-type AED 100 and/or the first medical server 820 through the wireless network 810. For example, a health insurance corporation and/or an insurance company may manage the second medical server 850 and a database 855.

The wireless circuit 240 of the wearable patch-type AED 100 may transmit data HDATA corresponding to the ECG signals ECG1 and ECG2. The application may store a uniform resource locator (URL) of the first medical server 820 and/or a URL of the second medical server 850. Accordingly, the wireless circuit 240 of the wearable patch-type AED 100 may transmit data HDATA to the first medical server 820 (S801) and/or the second medical server 850 (S821) through the network 810 under the control of the CPU 230A or 230B or a control of an application performed by the CPU 230A or 230B.

The data HDATA may include the ECG signals ECG1 and ECG2, data generated based on the ECG signals ECG1 and ECG2, and patient information. For example, data generated based on the ECG signals ECG1 and ECG2 may include data on ventricular fibrillation, data on ventricular tachycardia, a heart rate, arrhythmia, or a defibrillation history, but is not limited thereto.

The wireless network 810 may transmit the data HDATA to the first medical server 820 and/or the second medical server 850 (S803 and/or S821). The first medical server 820 may store the data HDATA in the database 821 (S804), and transmit the data HDATA to a computing device 845 of a doctor through the network 830 (S805). For example, the computing device 845 of a doctor may be a PC or a tablet PC, but is not limited thereto. The doctor may work at a medical institution, a public health care center, a clinic, a hospital, or a rescue center.

The doctor may diagnose a state of a patient using the data HDATA displayed through the computing device 845 and input diagnostic data into the computing device 845 (S807). The computing device 845 transmits the diagnostic data DDATA to the first medical server 820 through the network 830 (S809), and the first medical server 820 stores the diagnostic data DDATA in the database 821 (S804) and transmits the diagnostic data DDATA to the network 810 (S811). The network 810 may transmit the diagnostic data DDATA to the wearable patch-type AED 100 (S813) or to the second medical server 850 (S821). The patch-type AED 100 may store the diagnostic data DDATA in the memory 241 or may output the diagnostic data DDATA through the alarm 247. The second medical server 850 may store the diagnostic data DDATA in the database 855 (S823).

Each of the servers 820 and 850 may store or analyze each of the data HDATA and DDATA in the databases 821 and 855. Moreover, each of the servers 820 and 850 may transmit a result of the analysis to the networks 810 and 830.

Figure 15:
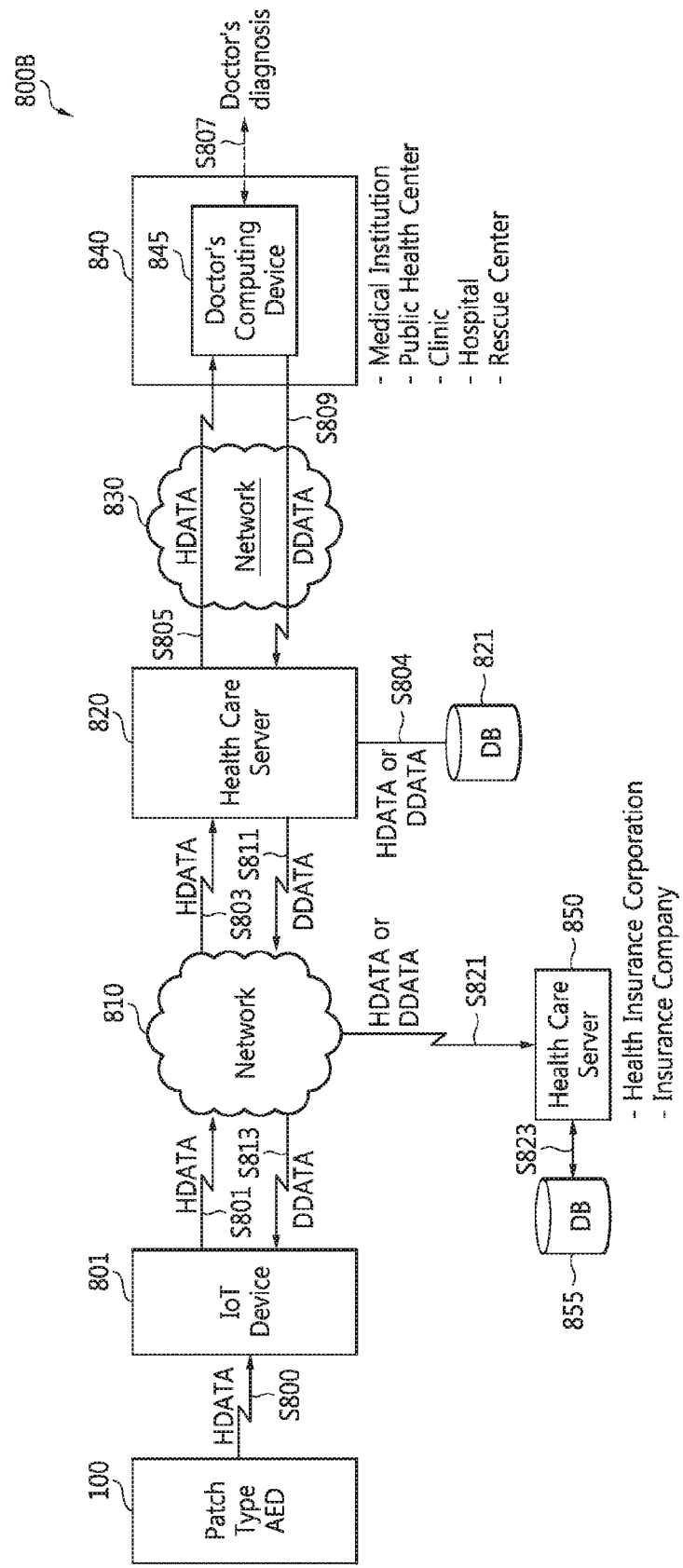

Referring to FIG. 15, a data processing system 800B may be used to provide a remote medical service. The data processing system 800B may include the wearable patch-type AED 100, an IoT device 801, and the first medical server 820 which can communicate with the IoT device 801 through the wireless network 810. The IoT device 801 may be the smart device 400 or 700 of the examples shown in and described with reference to FIG. 5, 9, 12, or 13, but is not limited thereto. The data processing system 800A of FIG. 14 is similar to the data processing system 800B of FIG. 15, in terms of its structure and operation, except for the IoT device 801 through which the wearable patch-type AED 100 transmits or receives data to or from the wireless network 810.

The wearable patch-type AED 100 may transmit data HDATA generated by the wearable patch-type AED 100 to the IoT device 801 (S800). For example, the wearable patch-type AED 100 may automatically transmit the data HDATA to the IoT device 801 according to a request of the IoT device 801 or when an abnormality is detected in the heart function of a patient (S800). The IoT device 801 may transmit the data HDATA to the network 810 (S801), and receive diagnostic data DDATA output from the network 810. The IoT device 801 may display the diagnostic data DDATA on a display of the IoT device 801. Accordingly, a user of the IoT device 801 may provide appropriate medical care to or perform first aid on a patient who wears the wearable patch-type AED 100, using the diagnostic data DDATA.

Figure 16:
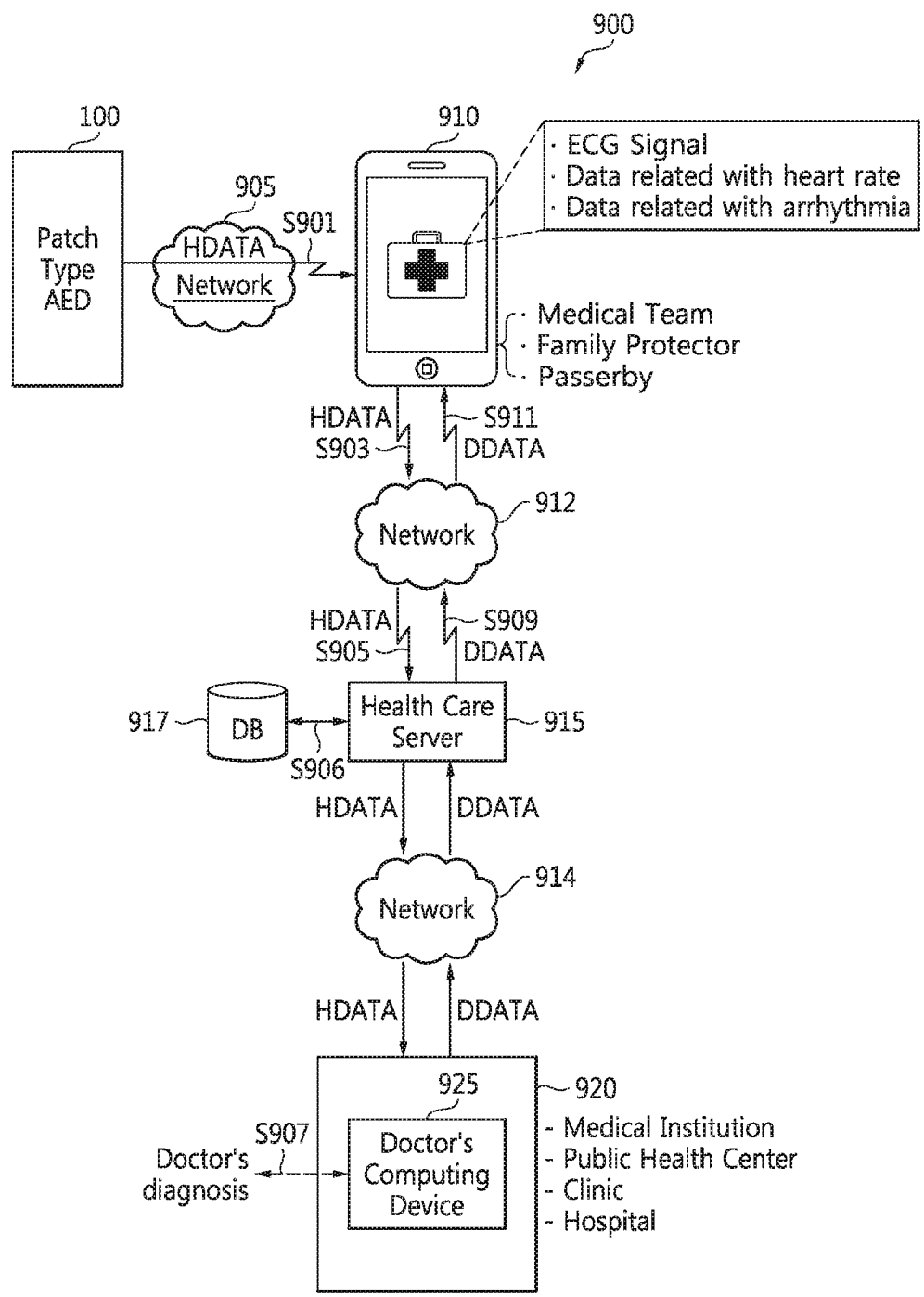

Referring to FIG. 16, a data processing system 900 may be used to provide a remote medical service. The data processing system 900 may include the wearable patch-type AED 100 and a mobile computing device 910 which can communicate with the wearable patch-type AED 100 through a network 905. The data processing system 900 may further include a medical server 915 which can communicate with the mobile computing device 910 through a network 912.

The wireless circuit 240 of the wearable patch-type AED 100 may transmit data HDATA corresponding to the ECG signals ECG1 and ECG2 to the mobile computing device 910 through the network 905 under the control of the CPU 230A or 230B or a control of an application performed by the CPU 230A or 230B (S901).

For example, the mobile computing device 910 may be a smart phone, a tablet PC, an MID, a IoT device, or a IoE device, but is not limited thereto. A user of the mobile computing device 910 which can perform an application to be described with reference to FIG. 16 may be a medical team, a guardian, or a passerby. The passerby preferably has completed first aid training.

An application performed by a CPU of the mobile computing device 910 may be represented by an icon(s), interface, etc. displayed on a display device. The mobile computing device 910 may transmit the data HDATA to the medical server 915 through the network 912 under the control of the application (S903 and S905). The mobile computing device 910 stores a URL of the medial server 820, such that the mobile computing device may transmit the data HDATA to the medical server 915 corresponding to a URL under the control of an application (S903 and S905).

The medical server 915 may store the data HDATA in the database 917 (S906), and transmit the data HDATA to a computing device 925 of a doctor working at a medical institution 920 through the network 914.

The doctor may diagnose a state of a patient using the data HDATA displayed through the computing device 925 and input diagnostic data into the computing device 925 (S907). The computing device 925 may transmit the diagnostic data DDATA to the medical server 915 through the network 914, and the medical server 915 may store the diagnostic data DDATA in the database 917 (S906), and transmit the diagnostic data DDATA to the mobile computing device 910 through the network 912 (S909 and S911). The mobile computing device 910 may display the diagnostic data DDATA of the doctor on a display of the mobile computing device 910. Accordingly, a user of the mobile computing device 910 may provide appropriate medical care to or perform first aid on a patient who wears the wearable patch-type AED 100, using the diagnostic data DDATA.

Figure 17:
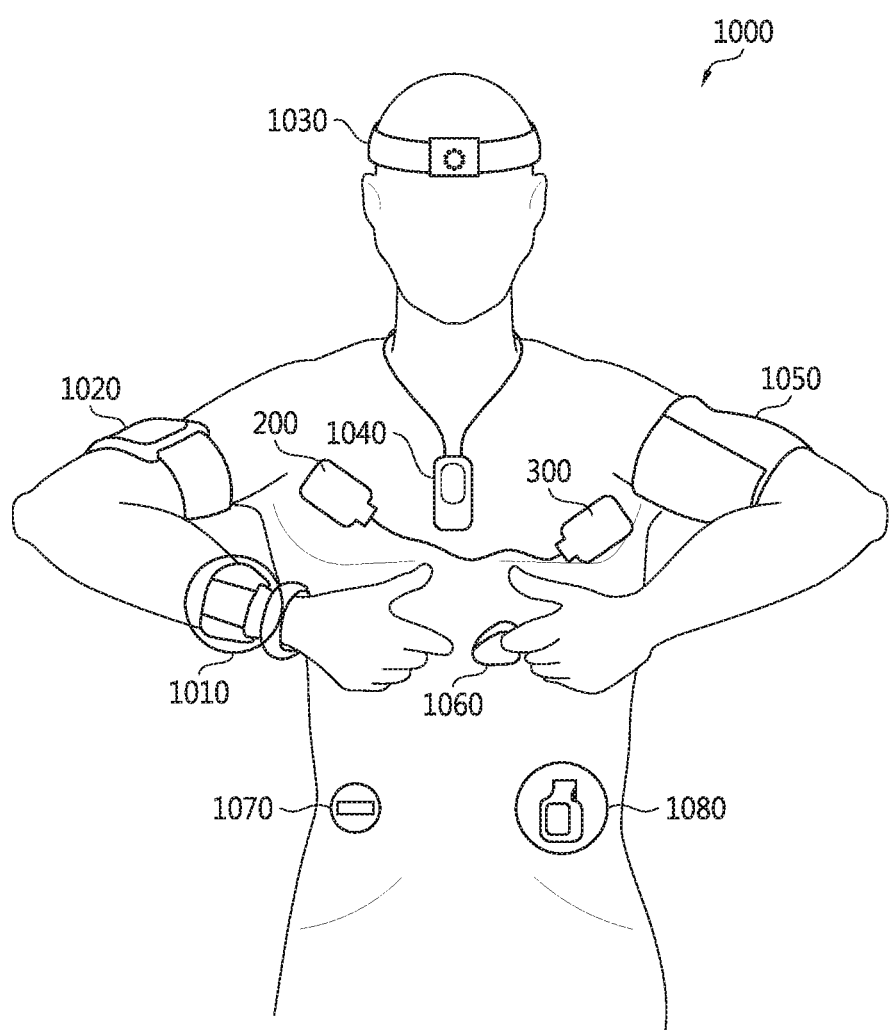

Referring to FIG. 17, a data processing system 100 may be a wireless sensor network (WSN). The data processing system 1000 may include a wearable patch-type AED and any one or more of various different types of IoT devices. Eight different types of IoT devices are given by way of example in FIG. 17, i.e., as first through eighth IoT devices 1010, 1020, 1030, 1040, 1050, 1060, 1070, and 1080.

In FIG. 17, the first IoT device 1010 is a smart watch, the second IoT device 1020 comprises a calorie sensor, the third IoT device 1030 comprises a sleep sensor to induce sleep, the fourth IoT device 1040 comprises a fall detection sensor, the fifth IoT device 1050 comprises a stress detection sensor, the sixth IoT device 1060 comprises an oxygen saturation ($SpO_2$) sensor, the seventh IoT device 1070 comprises a skin temperature sensor, and the eighth IoT device 1080 is a pedometer.

When the wearable patch-type AED performs a defibrillation operation on a patient, two or more of the IoT devices 1010, 1020, 1030, 1040, 1050, 1060, 1070, and 1080 may transmit or receive a sensing signal sensed from the patient to or from each other. For example, when the first IoT device 1010 comprises a sink node and any other of the IoT device(s) 1020, 1030, 1040, 1050, 1060, 1070, and 1080 comprises a sensor node, data HDATA output from the wearable patch-type AED and a sensor signal output from the IoT device(s) 1020, 1030, 1040, 1050, 1060, 1070, and 1080 may be transmitted to the first IoT device 1010. The first IoT device 1010 may transmit the data HDATA and each sensor signal to the smart device 400 or 700.

In a WSN, a sink node is also referred to as a base station, functions as a gateway which connects the WSN and an external network (for example, the internet), assigns a task to each sensor node, and collects an event sensed by the each sensor node. In the WSN, a sensor node may be a node which can perform processing and gathering of sensory information, and the sensor node may be a node which can perform communication between nodes connected to each other in the WSN.

Figure 18:
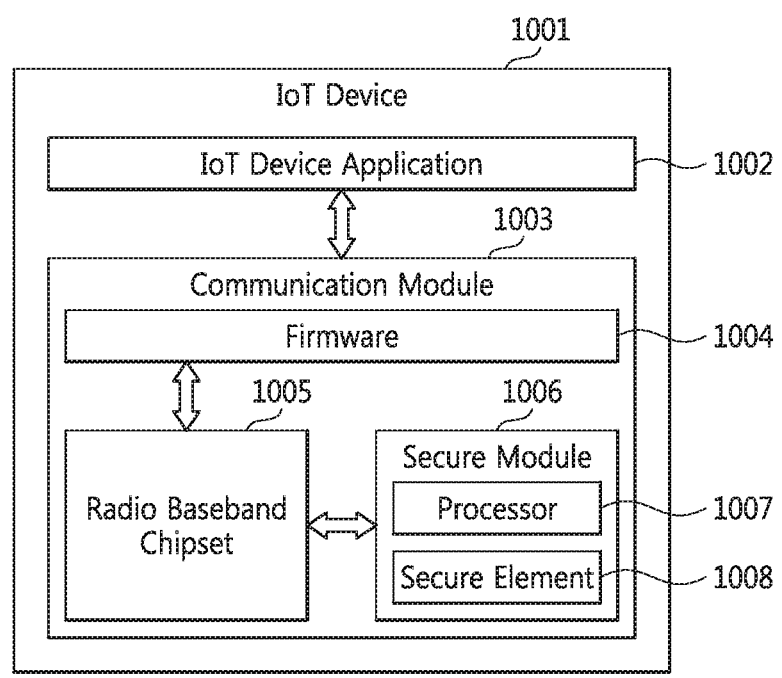
FIG. 18 is a block diagram of an example a smart device according to the present inventive concept.

FIG. 18 is a block diagram an example of a smart device according to the present inventive concept. Referring to FIGS. 1 to 18, a smart device 1001, e.g., an IoT device, may include an IoT device application 1002 and a communication module 1003. The communication module 1003 may include firmware 1004, a radio baseband chipset 1005, and a secure module 1006.

The IoT device application 1002 may comprise software that controls the communication module 1003, and may be performed by a CPU. The communication module 1003 may be a LAN, a WLAN such as Wi-Fi, a WPAN such as Bluetooth, a wireless USB, a Zigbee, an NFC, an RFID, or a wireless communication component which is connected to a mobile communication network, to transmit and receive data to and from the mobile communication network.

The firmware 1004 may provide the IoT device application 1002 and an API, and may control the wireless band chipset 1005 under the control of the IoT device application 1002. The radio baseband chipset 1005 may provide connectivity to a wireless communication network. The secure module 1006 may include a processor 1007 and a secure element 1008. The secure module 1006 may authenticate an IoT device for a connection to the wireless communication network, and authenticate the IoT device for access to a wireless network service.

The secure module 1006, which includes the processor 1007 and the secure element 1008, may be provided as a single package, and the processor 1007 and the secure element 1008 may transmit or receive an instruction and/or data to or from each other through an internal bus. The secure element 1008 may offer a defense against an attack from the outside, i.e., may comprise a firewall. Accordingly, the secure element 1008 may safely store confidential data, e.g., data related to patient information or ECG signals ECG1 and ECG2.

The IoT device 1001 shown in FIG. 18 is exemplary of one (FIG. 17) that can be employed in combination with a wearable patch type AED according to the inventive concept. That is, any of the IoT devices 1010, 1020, 1030, 1040, 1050, 1060, 1070, and 1080 may include components corresponding to the components 1002 and 1003. The IoT device application 1002 may be performed by the CPU 230A or 230B, and the communication module 1003 may correspond to the wireless circuit 240.

In other examples of the systems that include a smart device in combination with an AED according to the inventive concept, such as any of the systems including the smart devices 400, 510, 700, 801, 910 described above, the smart device may include components corresponding to the components 1002 and 1003.

As described above, a wearable patch-type automatic defibrillator including a battery may be worn near the heart of a patient all day long, and may analyze an electrocardiogram of the patient in real time and automatically provide the patient with an electrical shock instantly when defibrillation is required according to a result of the analysis. Accordingly, the wearable patch-type automatic defibrillator may increase the survival rate of a heart patient especially in the case in which the patient experiences cardiac arrhythmias severe enough to cause the patient to become rather incapacitated, e.g., when the cardiac arrhythmias are severe enough to cause the patient to collapse.

Although examples of the present inventive concept have been shown and described, it will be appreciated by those skilled in the art that changes may be made to these examples without departing from the principles and spirit of the inventive concept, the scope of which is defined in the appended claims.

What is claimed is:

1. A wearable automated external defibrillator (AED) comprising:
   a battery having a capacity to store electrical energy for defibrillation;
   a controller operatively electrically connected to the battery, and configured to control a discharging of the battery; and a first electrode and a second electrode operatively electrically connected to the battery and the controller, wherein the battery, the controller, the first electrode and the second electrode are integral and collectively constitute a skin patch sized and shaped to be worn by a patient on a region of the patient adjacent the heart of the patient, wherein the first and second electrodes are disposed in the skin patch at locations at which the first and second electrodes are configured to detect electrical activity of the heart when the skin patch is worn on the region of the patient adjacent the heart of the patient, wherein the first and second electrodes are configured to transmit ECG signals representative of the electrical activity of the heart of the patient wearing the AED, and wherein the controller is configured to automatically connect a first terminal of the battery to the first electrode and a second terminal of the battery to the second electrode in a defibrillation mode thereby providing electrical energy stored in the battery to the first and second electrodes, the defibrillation mode being triggered when an analysis of ECG signals received through the at least one electrode indicates the patient wearing the AED requires defibrillation.

2. The wearable AED of claim 1, wherein the controller is configured to analyze ECG signals received through the first and second electrodes and assume said defibrillation mode when an analysis of ECG signals by the controller indicates the patient wearing the AED requires defibrillation.

3. The wearable AED of claim 1, wherein the controller includes a fall detector operative to detect that the patient is falling down and generate a detection signal indicative of the falling down of the patient, and the controller is configured to automatically provide the patient with the electrical energy stored in the battery through the at least one defibrillation electrode when both the detection signal has been generated and the analysis of the ECG signals indicates the patient wearing the AED requires defibrillation.

4. The wearable AED of claim 1, wherein the controller includes:

a fall detector operative to detect that the patient is falling down and generate a detection signal indicative of the falling down of the patient;

a CPU configured to analyze a heart rhythm of the patient using ECG digital signals related to the ECG signals and generate a control signal based on a result of the analysis and the detection signal; and a defibrillator circuit configured to automatically connect the first terminal of the battery and the first electrode, and the second terminal of the battery and the second electrode so as to provide the patient with a shock in response to the control signal.

5. The wearable AED of claim 2, wherein the controller includes a wireless circuit configured to convert data related to the result of the analysis into wireless data and transmit the wireless data to an external wireless device.

6. The wearable AED of claim 2, wherein the first and second electrodes are disposed in the skin patch at locations, respectively, spaced apart from one another such that the first electrode is configured to transmit a first ECG signal representative of the electrical activity of the heart of the patient wearing the AED and the second electrode is configured to transmit a second ECG signal representative of the electrical activity of the heart of the patient wearing the AED, and the controller includes:

an ECG sensor chip configured to generate ECG output signals corresponding to a difference between the first and second ECG signals, an analog-to-digital converter operatively connected to the ECG sensor chip to convert the ECG output signals into ECG digital signals, a CPU configured to analyze a heart rhythm of the patient using the ECG digital signals and generate a control signal based on a result of the analysis, a wireless circuit operatively connected to the CPU and configured to convert data output from the CPU and related to the heart rhythm into wireless data, and a defibrillator circuit operatively connected to the CPU and the battery and configured to automatically connect the first terminal of the battery and the first electrode, and the second terminal of the battery and the second electrode so as to provide the patient with a shock in response to the control signal.

7. The wearable AED of claim 2, wherein the controller includes:

a security circuit operatively connected to the CPU and configured to convert data output from the CPU and related to the result of the analysis into security data, and a wireless circuit operatively connected to the security circuit and configured to convert the security data into wireless data.

8. The wearable AED of claim 2, wherein the controller includes:

a CPU configured to determine, based on the result of the analysis, whether the controller is malfunctioning and to generate a control signal according to a result of the determination, and a defibrillator circuit operatively connected to the CPU and configured to automatically connect the first terminal of the battery and the first electrode, and the second terminal of the battery and the second electrode so as to provide the patient with a shock in response to the control signal.

9. A wearable automated external defibrillator (AED), comprising:

a first AED pad including:

a first battery having a capacity to store electrical energy for defibrillation of a patient who wears the AED, a first electrocardiogram (ECG) electrode, and a first defibrillation electrode;

a second AED pad which includes a second ECG electrode and a second defibrillation electrode;

a controller operatively connected to the first ECG electrode, the second ECG electrode and the first defibrillation electrode and the first battery, and including:

an ECG sensor chip configured to generate ECG output signals based on a first signal output from the first ECG electrode and a second signal output from the second ECG electrode, an analog-to-digital converter operatively connected to the ECG sensor chip to receive the ECG output signal from the ECG sensor chip and convert the ECG output signals into ECG digital signals, a CPU operatively connected to the analog-to-digital converter to receive the ECG output signals therefrom, the CPU being configured to analyze the ECG digital signals and generate, as a result of the analysis, data representative of a heart rhythm of the patient, the data including a control signal when an abnormality in the heart rhythm is detected from the analysis of the ECG digital signals, a wireless circuit operatively connected to the CPU to receive the data generated by the CPU and configured to convert the data received from the CPU into wireless data, and a defibrillator circuit configured to automatically electrically connect the first battery and the first defibrillation electrode in response to the control signal such that the first battery provides the patient with a shock through the first defibrillation electrode; and a cable which connects the first AED pad and the second AED pad, and wherein the defibrillator circuit is configured to automatically connect a second terminal of the first battery and the second defibrillation electrode through the cable in response to the control signal.

10. The wearable AED of claim 9, wherein the second AED pad further includes a second battery which is connected to the first battery in series through the cable.

11. The wearable AED of claim 9, wherein the first AED pad includes:

a second battery operatively connected to the controller to supply an operation voltage to the controller; and a ground electrode electrically connected to the controller.

12. The wearable AED of claim 9, wherein the first battery is a flexible battery, and the defibrillator circuit is configured to control a charging and discharging of the flexible battery.

13. An external defibrillator comprising:

first and second pads configured for attachment to a skin of a patient at regions, respectively, near the heart of the patient; and cable running between the first and second pads, wherein the second pad includes a battery having a capacity to store electrical energy for defibrillation, the first pad includes a controller operatively electrically connected to the battery via the cable, and configured to control a discharging of the battery, and the first pad includes an electrode operatively connected to the controller to transmit first ECG signals to the controller representative of electrical activity of the heart, the second pad includes an electrode electrically connected to the controller via the cable to transmit second ECG signals to the controller representative of electrical activity of the heart, the first pad includes an electrode operatively connected to the battery, and the second pad includes an electrode operatively connected to the battery, and the controller is configured to automatically provide, in a defibrillation mode, electrical energy stored in the battery to the electrodes of the first and second pads that are operatively connected to the battery, the defibrillation mode being triggered when an analysis of ECG signals received by the controller indicates the patient wearing the skin patch requires defibrillation.

14. The defibrillator of claim 13, wherein the first pad includes an ECG electrode operatively connected to the controller to transmit the first ECG signals to the controller, and a first defibrillation electrode operatively connected to the battery via the cable to receive electrical energy stored in the battery when the controller is in the defibrillation mode, and the second pad includes an ECG electrode electrically connected to the controller via the cable to transmit the second ECG signals to the controller, and a second defibrillation electrode operatively connected to the battery to receive electrical energy stored in the batter when the controller is in the defibrillation mode.

15. The defibrillator of claim 13, wherein at least one of the first and second pads includes a common electrode that is both operatively connected to the controller to transmit ECG signals to the controller, and is connected to the battery to receive electrical energy stored in the battery when the controller is in the defibrillation mode.

16. The defibrillator of claim 13, wherein the controller is configured to analyze the first and second ECG signals and assume the defibrillation mode when an analysis of ECG signals by the controller indicates the patient wearing the external defibrillator requires defibrillation.

17. The defibrillator of claim 16, wherein the controller includes a wireless circuit configured to convert data of the analysis into wireless data and transmit the wireless data to an external wireless device.

18. The defibrillator of claim 13, wherein the controller includes a fall detector operative to detect that the patient is falling down and generate a detection signal indicative of the falling down of the patient, and the controller is configured to be capable of assuming the defibrillation mode based on a determination of whether the detection signal has been generated.

* * * * *